United States Patent [19]
Yang

[11] Patent Number: 5,664,938
[45] Date of Patent: Sep. 9, 1997

[54] MIXING APPARATUS FOR MICROFLOW GRADIENT PUMPING

[76] Inventor: Frank Jiann-Fu Yang, 13983 Pike Rd., Saratoga, Calif. 95070

[21] Appl. No.: 393,449

[22] Filed: Feb. 23, 1995

Related U.S. Application Data

[63] Continuation-in-part of Ser. No. 114,497, Aug. 31, 1993, Pat. No. 5,630,706, which is a continuation of Ser. No. 847,654, Mar. 5, 1992, Pat. No. 5,253,981.

[51] Int. Cl.$^6$ ............................. F04B 39/10; F16K 15/14
[52] U.S. Cl. .................... 417/313; 137/114; 137/550; 137/512; 137/860; 137/565; 417/415; 366/273
[58] Field of Search ........................... 417/313, 415; 137/512, 550, 860, 612.2, 614.21, 614.2; 251/367; 366/273, 274

[56] References Cited

U.S. PATENT DOCUMENTS

| Re. 31,608 | 6/1984 | Magnussen, Jr. | 417/22 |
|---|---|---|---|
| 3,493,270 | 2/1970 | Doerfler | 137/493.9 |
| 3,572,651 | 3/1971 | Harker | 259/107 |
| 3,649,465 | 3/1972 | Scharf et al. | 435/302.1 |
| 3,680,981 | 8/1972 | Wagner | 417/388 |
| 3,929,320 | 12/1975 | Haller | 259/165 |
| 4,032,445 | 6/1977 | Munk | 210/103 |
| 4,035,168 | 7/1977 | Jennings | 55/67 |
| 4,045,343 | 8/1977 | Achener et al. | 210/101 |
| 4,128,476 | 12/1978 | Rock | 210/31 |
| 4,131,393 | 12/1978 | Magnussen, Jr. | 417/22 |

(List continued on next page.)

FOREIGN PATENT DOCUMENTS 4 032 82362  12/1991  Japan .

OTHER PUBLICATIONS

Ishii et al., "A Study Of Micro-High-Performance Liquid Chromatography", *Journal of Chromatography*, 144 (1977), pp. 157–168.

Ishii et al., "Studies Of Open-Tubular Micro-Capillary Liquid Chromatography", *Journal of Chromatography*, 185 (1979), pp. 73–78.

Schwartz et al., "A dual syringe LC solvent delivery system For Use With Microbore Columns", *American Laboratory*, Oct. 1984, 8 pages.

Scott et al., "Mode Of Operation And Performance Characteristics Of Microbore Col. For Use In Liquid Chromatography", *Journal of Chromatography*, 169 (1979) 51–72.

Snyder et al., "Reproducibility Problems in Gradient Elution Caused by Differing Equipment", *LC-GC*, vol. 8, No. 7, 10 pages.

Takeuchi et al., "Micro-High-Performance Liquid Chromatography With Long Micro-Packed Flexibe Fused-Solica Columns", *Journal of Chromatography*, 238 (1982) 409–418.

(List continued on next page.)

Primary Examiner—Timothy Thorpe
Assistant Examiner—Peter G. Korytnyk
Attorney, Agent, or Firm—Trask, Britt & Rossa

[57] ABSTRACT

An improved mixing unit and check valve for a fluid pumping system wherein gradient proportioning is performed at high pressure are described. The mixing unit has lining means disposed on the inner surface of the chamber for preventing frictional contact between the steel of the chamber and the surface of the rotor. The lining means is formed of a polymeric material selected for frictional compatibility with the rotor, and avoids formation of undesirable particulates by friction with the rotor surface. The check valve has a poppet comprising a midsection dimensioned to provide forward and rearward surfaces against which fluid flow will exert force, a first arm extending transversely from the midsection first side toward the valve inlet, a second arm extending transversely from the midsection second side toward the valve outlet, and first and second resilient seals respectively annularly disposed about the first and second arms. The resilient seals are formed of a resiliently compressible material, and have an uncompressed thickness which is somewhat greater than the first arm length.

24 Claims, 12 Drawing Sheets

U.S. PATENT DOCUMENTS

| | | | |
|---|---|---|---|
| 4,180,375 | 12/1979 | Magnussen, Jr. | 417/22 |
| 4,233,156 | 11/1980 | Tsukada et al. | |
| 4,260,342 | 4/1981 | Leka et al. | 417/458 |
| 4,271,697 | 6/1981 | Mowery, Jr. | |
| 4,311,586 | 1/1982 | Baldwin et al. | |
| 4,347,131 | 8/1982 | Brownlee | 210/101 |
| 4,422,942 | 12/1983 | Allington . | |
| 4,483,733 | 11/1984 | Sato et al. | 156/541 |
| 4,496,245 | 1/1985 | Conrad et al. | |
| 4,599,045 | 7/1986 | Slough | 417/44 |
| 4,649,118 | 3/1987 | Anderson | 435/316 |
| 4,673,000 | 6/1987 | Haerr et al. | 137/860 |
| 4,711,764 | 12/1987 | Good | 422/65 |
| 4,714,545 | 12/1987 | Benk et al. | |
| 4,728,434 | 3/1988 | Trafford | 210/656 |
| 4,775,481 | 10/1988 | Allington | 210/656 |
| 4,797,207 | 1/1989 | Hoganen et al. | |
| 4,832,575 | 5/1989 | Miller et al. | |
| 4,862,911 | 9/1989 | Yie | 137/454.4 |
| 4,869,374 | 9/1989 | Allington | 210/198 |
| 4,883,409 | 11/1989 | Strohmeier et al. | |
| 4,980,059 | 12/1990 | Barlow et al. | |
| 4,981,597 | 1/1991 | Allington et al. | |
| 5,040,126 | 8/1991 | Allington . | |
| 5,089,124 | 2/1992 | Mahar et al. | |
| 5,127,437 | 7/1992 | Ross, II | 137/614.18 |
| 5,132,014 | 7/1992 | Allington et al. | 210/634 |
| 5,158,675 | 10/1992 | Allington et al. | |
| 5,312,233 | 5/1994 | Tanny et al. | |
| 5,360,320 | 11/1994 | Jameson et al. | |

OTHER PUBLICATIONS van der Wal et al., "Gradient Elution System for Capillary and Micro HPLC", *Journal of High Resolution Chromatography & Chromatography Communications*, vol. 6, Apr. 1983, pp. 216–217.

Yang, Frank J., "Fused–Silica Narrow–Bore Microparticle–Packed–Col.–High–:erformance Liquid Chromatography", *Journal of Chromatography*, 236 (1982) 265–277.

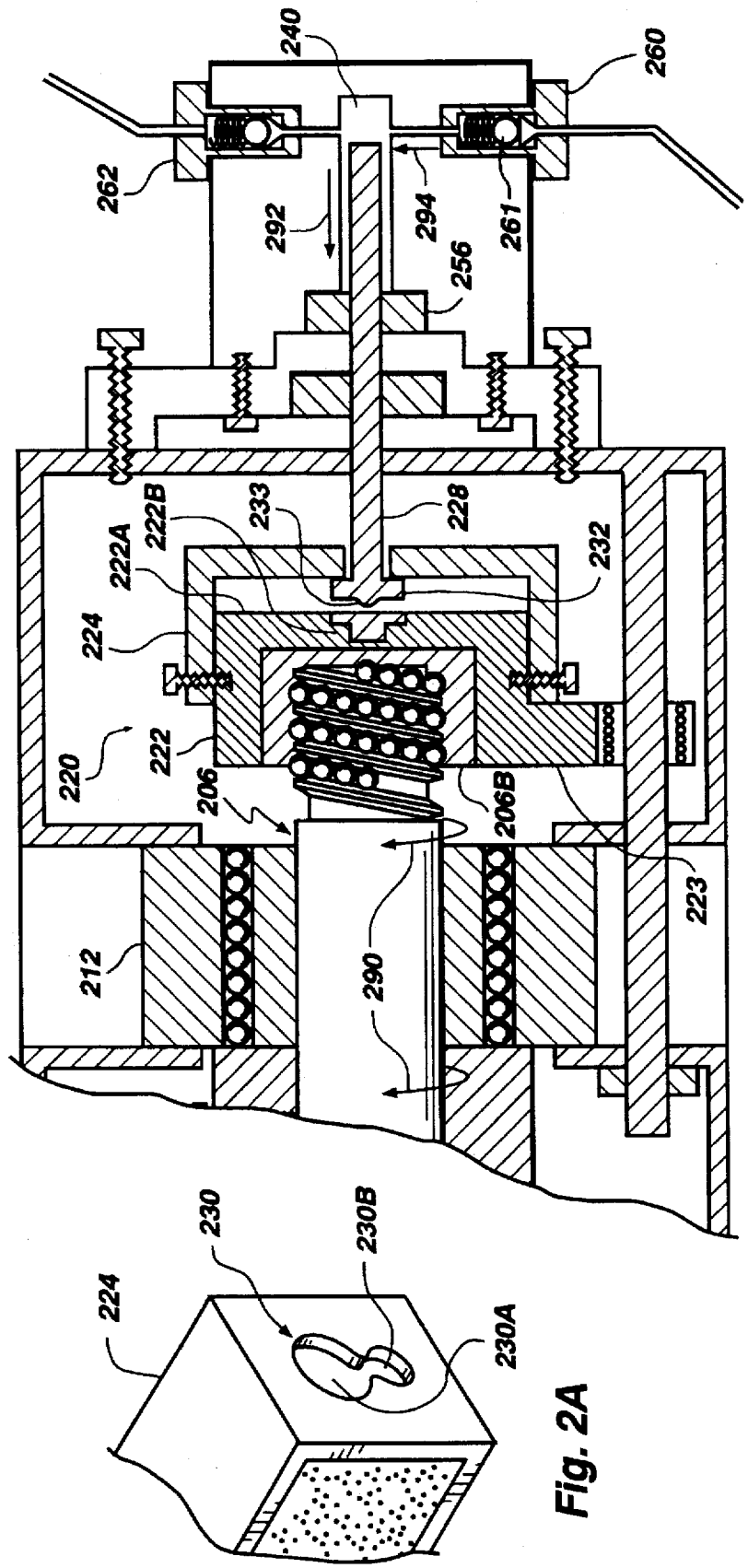

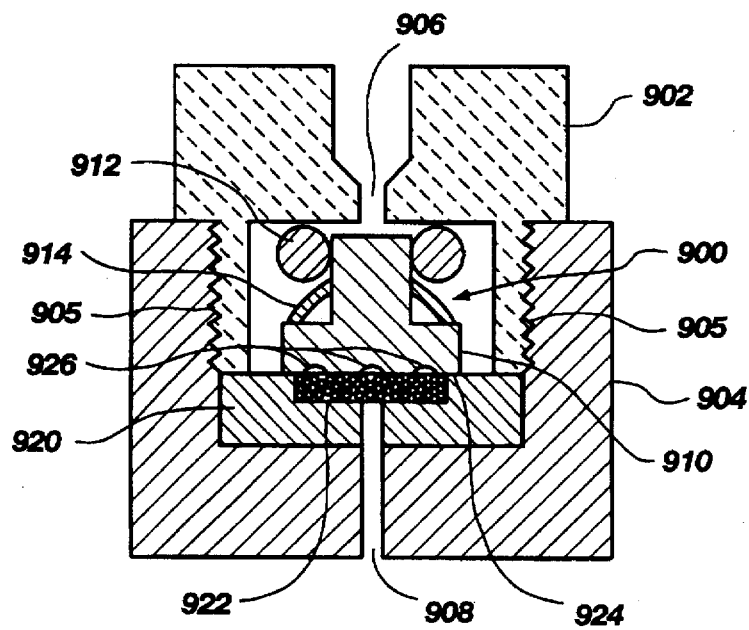
Fig. 9
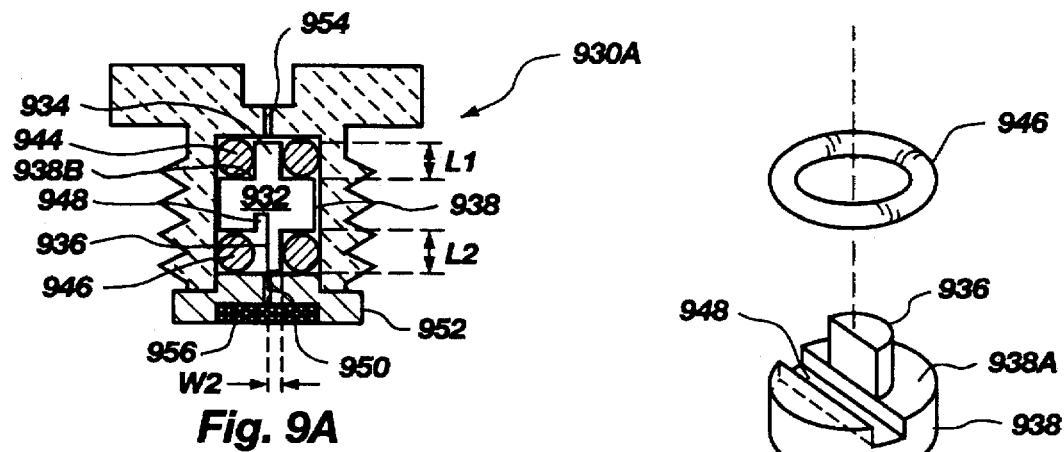
Fig. 9A
Fig. 9B
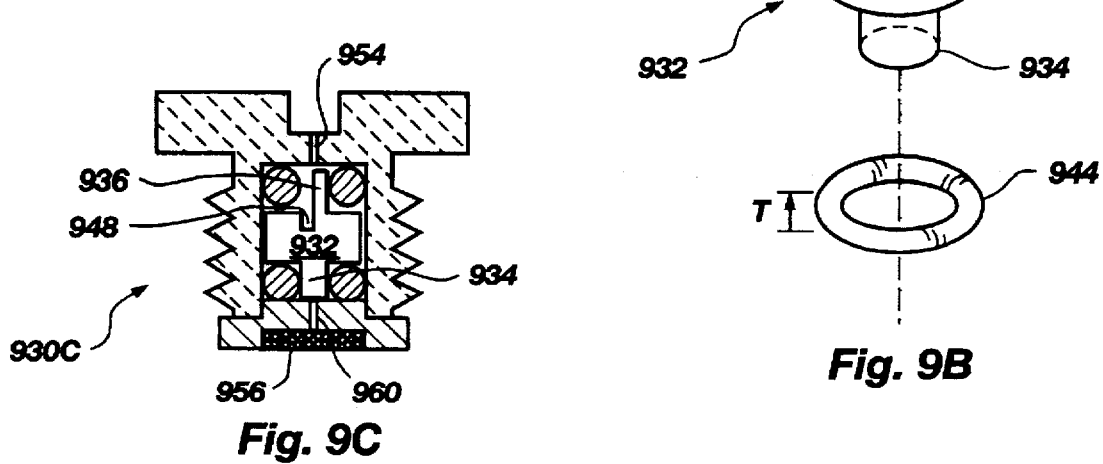
Fig. 9C

MIXING APPARATUS FOR MICROFLOW GRADIENT PUMPING

RELATED APPLICATIONS

This application is a continuation-in-part of U.S. Ser. No. 08/114,497 filed on Aug. 31, 1993 now U.S. Pat. No. 5,630,706 which is a continuation of U.S. Ser. No. 07/847,654 filed on Mar. 5, 1992, now U.S. Pat. No. 5,253,981, issued Oct. 19, 1993.

BACKGROUND OF THE INVENTION

1. Field

The invention relates to high-pressure fluid pumping systems, and more particularly to pump systems for HPLC and other chemical and biological analytical procedures.

2. State of the Art

Fluid pumping systems for high-pressure liquid chromatography (referred to hereinafter as HPLC) and the like are well known. In HPLC, a sample is applied to the top of a column which is packed with particles of a selected size and composition, and a solvent or solvent mixture is pumped through the column. Chemical components of the sample are eluted in the solvent from the lower end of the column at different times in a manner which reflects their chemical properties and composition. For reproducibility and high analytical accuracy, HPLC requires fluid pumping which is stable and essentially pulseless (smooth flow which does not vary during fill and pump strokes), with defined precise flow rates.

A common technique used to enhance separation of compounds by HPLC is to use two or more solvents and to vary the relative amounts of the solvents in the solvent mixture as it is being pumped through the column. This technique is often referred to as gradient separation or gradient HPLC. Formation of the gradient requires mixing of the two solvents in a controlled fashion prior to injecting the solvent mixture into the column. Typical prior art HPLC pumping systems use one of two main arrangements for mixing the solvents, as exemplified in U.S. Pat. Nos. 4,311,586 to Baldwin et al., and 4,714,545 to Bente et al. In both arrangements, the solvents are mixed together before entering the pump which pumps the mixture into the column.

A development of importance in the area of HPLC is the use of so-called "microbore" columns having an internal diameter (abbreviated herein as I.D.) of 1 millimeter or less. (See R. Scott and P. Kucera, *J. Chromatogr.* 169:51, 1979; F. Yang, *J. Chromatogr.* 236: 265, 1982; F. Yang, U.S. Pat. No. 4,483,733, (November 1984); D. Ishii et al., *J. Chromatogr.* 144: 157, 1977; D. Ishii et al., *J. Chromatogr.* 185: 73, 1979; T. Takeuchi et al., *J. Chromatogr.* 238: 409, 1982.) The advantages of microbore column HPLC over conventional HPLC include reductions of up to 100-fold each in the amounts of solvent and column packing required. Such reductions bring corresponding reduction not only in the initial cost of solvent and expensive column packing material, but in the amount of solvent which must be disposed of after use. Since many of the solvents used in HPLC have toxic components, the environmental benefit of microbore HPLC vs. conventional HPLC is substantial. Additionally, there are numerous advantages for various analytical procedures (see above references).

Instrumentation for micro-bore HPLC has been developed by several LC instrument manufacturers. The typical "1.0 mm. id. micro-HPLC pump" systems presently commercially available are modified versions of conventional low pressure proportioning HPLC gradient pumps (See H. Bente, et al. U.S. Pat. No. 4,714,545 (December 1987); G. Leka et al., U.S. Pat. No. 4,260,342, (April 1981); P. Trafford, U.S. Pat. No. 4,728,434 (March 1988); P. Achener, et al., U.S. Pat. No. 4,045,343 (August 1977); J. Rock, U.S. Pat. No. 4,128,476 (December 1978); H. Magnussen, Jr. U.S. Pat. No. 4,180,375 (December 1979); H. Magnussen, Jr., U.S. Pat. No. 4,131,393, (December 1978); R. Allington, U.S. Pat. No. 4,869,374 (September 1989). Such conventional systems use cam-driven pumps in which each solvent is drawn separately into the piston chamber by the fill stroke of the pump. Mixing occurs by turbulence during the fill stroke and/or by pumping the mixed fluids through a mixing unit before injecting it into the column. It is highly desirable to have the fill stroke extremely short in comparison to the pump stroke (U.S. Pat. No. 4,311,586 to Baldwin et al.). With cam-driven pumps, the desired ratio of the fill stroke to the total cycle is achieved by selecting the shape and dimensions of the cam.

However, it is difficult to dimensionally adapt such cam-driven pump designs to provide both low flow rates under high pressure and a very low fill stroke/stroke cycle ratio. As a practical matter, cam-driven pumps with the desired stroke ratios cannot be designed for flow rates lower than about 50 µl per minute. Also, cams for these low flow rates are quite large, increasing the bulk of the pump which must be used within a relatively small area crowded with other apparatus.

Therefore, the modified conventional systems referred to in the preceding paragraph for microbore applications provide a lower flow rate to individual columns either by the split-flow technique (Sj. van der Wal et al., *J. High Resolut Chromatogr. Commun.* 6:216, 1983), or by reducing the volume of the piston chamber.

Unfortunately, such modified low pressure proportioning pump systems operate poorly at flow rates below 50 µl/min in gradient HPLC with microbore columns. There are three major problem areas. First, the sum of the system volume including proportioning valves, piston chamber, inlet check valve and interface tubings is typically five to ten time greater than the amount of solvent eluted per minute, which places a lower limit on the minimum gradient step obtainable. For typical example, there may be a 100 µl total system volume for a system operating at 10 µl per minute. In this case, it takes about ten minutes for every gradient step change. Such a large minimum step provides very poor resolution for linear gradient elution.

Second, again because of the relatively large system volume, there is a long gradient delay time. Because the mixed solvent at the outlet cavity of the proportioning valves must travel through a piston chamber having a large liquid-end volume, in addition to the above-mentioned components, the effective gradient elution of the sample components in the column is delayed a long time. A typical pump liquid end volume of 2 ml therefore causes about 200 minutes gradient delay when operated at a column elution rate of 10 µl/min.

The long delay times and the relatively large gradient steps are not only time-consuming for the user, but also allow significant diffusion of the solvents in the gradient to occur. As a result of such diffusion, the gradients are generally poorly reproducible and sample components are poorly separated (L. Snyder et al., "Reproducibility problems in gradient elution caused by differing equipment," LC-GC, Vol. 8, No. 7, p. 524, 1990).

A further disadvantage is that the gradient regeneration time is very long. A volume approximately three times that of the pump liquid end is required for purging and regeneration of the initial solvent composition. For the 2 ml liquid end volume of the previous example above, it will take 600 minutes to regenerate the initial solvent composition at a 10 μl/minute elution rate.

One typical approach to alleviating these problems of cam-driven pumps at low flow rates is the split flow technique. The solvent gradient is generated at high flow rate to eliminate the problem of gradient delay. A microflow stream is then split at constant pressure from the main solvent stream and sent to the injector and column; the excess flow is usually discarded. Thus, the split-flow technique does not offer any reduction in solvent use over conventional methods. Also, because the gradient is split at constant pressure, the actual pressure in the microflow column has diminished stability and accuracy.

A further disadvantage of cam-driven pumps is that a single pump can only provide a limited range of flow rates. This is because different flow rate ranges require cams of substantially different size, and the position of the cam relative to the motor and the piston is determined by the cam dimensions. Changing the positions of the motor and piston to accommodate a cam of different size is impractical because of the sensitive alignment required in piston pumps.

An alternate approach for pumping in microbore column HPLC is the single-stroke syringe-type piston pump (M. Munk, U.S. Pat. No. 4,032,445 (June 1977), R. Brownlee, U.S. Pat. No. 4,347,131 (August 1982), R. Alligton, U.S. Pat. No. 4,775,481 (March 1988). This type of syringe pump is capable of delivering solvent at a few μl/min. However, syringe-type pumps also have significant disadvantages for microbore gradient HPLC. First, it is difficult to maintain a constant flow rate during gradient elution, due to the continuously changing flow resistance. This variation in flow resistance is believed to be a consequence of solvent composition, solvent compressibility and syringe liquid volume changes. Second, it is necessary to refill the liquid phase in the syringe piston between each analysis to minimize solvent compressibility effect and ensure good flow rate reproducibility, but refilling of the syringe is generally slow. Third, for gradient elution multiple syringe pumps are required, and these are very costly.

Because of these and other disadvantages of available low flow rate pumping systems, the potential advantages of microbore HPLC have not been realized.

Consequently, a need remains for a simple and inexpensive pump which can provide pulseless, reproducible solvent flow under pressures of up to 10,000 psi at flow rates of 0.1 to 1200 μl per minute or less. A need further remains for a pumping system having a greatly reduced liquid volume between the gradient mixing unit and the column injector, which can reproducibly provide gradient flows with small gradient steps and a short lead time.

A need also remains for a check valve which can provide fast and responsive action under very high pressures to reversals of flow pressure, and for mixing apparatus which does not cause produce particulates which can clog the flow stream at microflow rates. Still further, a need remains for a pump head check valve which is more durable under high pressures and does not need frequent replacement.

SUMMARY OF THE INVENTION

The invention comprises an improved mixing unit for a fluid pumping system wherein gradient proportioning is performed at high pressure. The mixing unit comprises a housing made of a first material, having an inner surface which defines a mixing chamber, an inlet for receiving fluid from an upstream fluid flow line, an outlet for discharging mixed fluid, a magnetic rotor whose exterior surface is formed of a second material, and lining means disposed on the inner surface of the chamber for preventing frictional contact between the first material and the second material. The lining means is formed of a polymeric third material selected for frictional compatibility with the second material, which does not cause undesirable particulates to be formed by friction with the surface of the rotor.

In further embodiments, the mixing unit is constructed for use with fluid pressure of up to at least about 10,000 psi within the mixing chamber and/or dimensioned for a fluid flow rate which is between about 0.1 μl per minute and about 20,000 μl per minute.

In a highly preferred embodiment, the mixing unit includes a novel high-pressure check valve installed in the inlet. The check valve comprises a valve housing defining a valve chamber with an inlet and an outlet, and poppet means disposed within the chamber for sealing against backflow while permitting flow in a forward direction. The poppet means comprises a midsection dimensioned to provide forward and rearward surfaces against which fluid flow will exert force, a first arm extending transversely from the midsection first side toward the valve inlet, a second arm extending transversely from the midsection second side toward the valve outlet, and first and second resilient seals respectively annularly disposed about the first and second arms. The resilient seals are formed of a resiliently compressible material, and have an uncompressed thickness which is somewhat greater than the first arm length.

The invention also embraces a pump including a wear-resistant check valve in the outlet. The wear-resistant check valve has fluid filtering means disposed to prevent particulates from entering the check valve from the piston chamber of the pump. In a highly preferred embodiment, the wear-resistant check valve is configured with the poppet means described in the preceding paragraph.

BRIEF DESCRIPTION OF THE DRAWINGS

In the figures, which depict what is presently regarded as the best mode for carrying out the invention, and wherein like reference numerals refer to like parts:

FIG. 2A is an oblique view of a preferred embodiment of a traveling piston bracket of the pump of FIG. 2;

FIG. 9 depicts a novel check valve useful in the pumping system of FIGS. 1 and 8;

FIG. 9A depicts an alternate embodiment of a check valve of the invention;

FIG. 9B is an elevational exploded view of the poppet means of the check valve of FIG. 9A;

FIG. 9C depicts an alternate embodiment of a check valve having the poppet of FIG. 9B;

DETAILED DESCRIPTION OF THE ILLUSTRATED EMBODIMENTS

Figure 1:
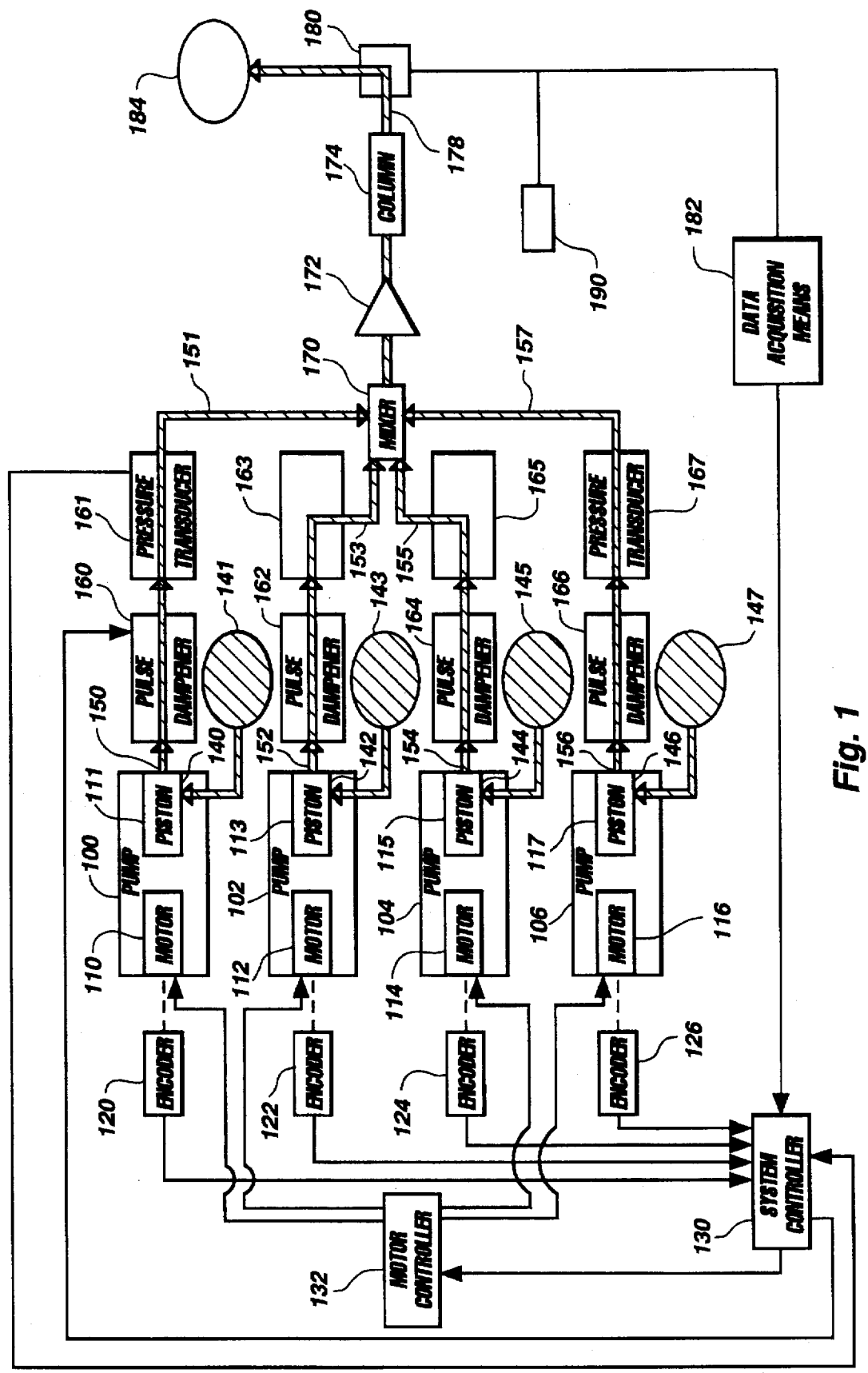
FIG. 1 is a block diagram setting forth the basic components of a multichannel pumping system having four pumping channels, with electrical communication indicated by a solid line, mechanical associations by a dashed line, and fluid flow shown as a hatched path.

FIG. 1 is a simplified block diagram depicting key components of a preferred embodiment of a pumping system having four individual pumps 100, 102, 104, 106. Preferred pumps for the system are the linear drive pump of FIG. 2, and are described in detail in reference thereto. However, other pumps may be substituted for the linear drive pump. For simplicity, therefore, only certain elements of the pump which are common to most piston and syringe-type pumps will be described in reference to FIG. 1.

Pumps 100, 102, 104, 106 each have a respective motor 110, 112, 114, 116, and a respective piston unit 111, 113, 115, 117. Each of motors 110, 112, 114, 116 is in electrical communication with a respective encoder 120, 122, 124, 126, which in turn communicate with pump system controller 130, embodied here as a personal computer. Encoders 120, 122, 124, 126 detect the rotation of their respective motors 110, 112, 114, 116, and provide rotation signals reflective thereof to pump system controller 130, which interprets the speed and position of the pump piston from the rotation signals. In the working embodiment, encoders 120, 122, 124, 126 are selected to be optical encoders integrally mounted to the individual motors. Pump system controller includes a standard digital motion control microprocessor (not shown); operation of the system controller will be described in greater detail later herein.

A motor controller 132 is connected to system controller 130 to receive motor control signals therefrom, which it then converts to motor operation signals. Motor controller 132 is further connected to send the motor operation signals to individual motors 110, 112, 114, 116.

Figure 2:
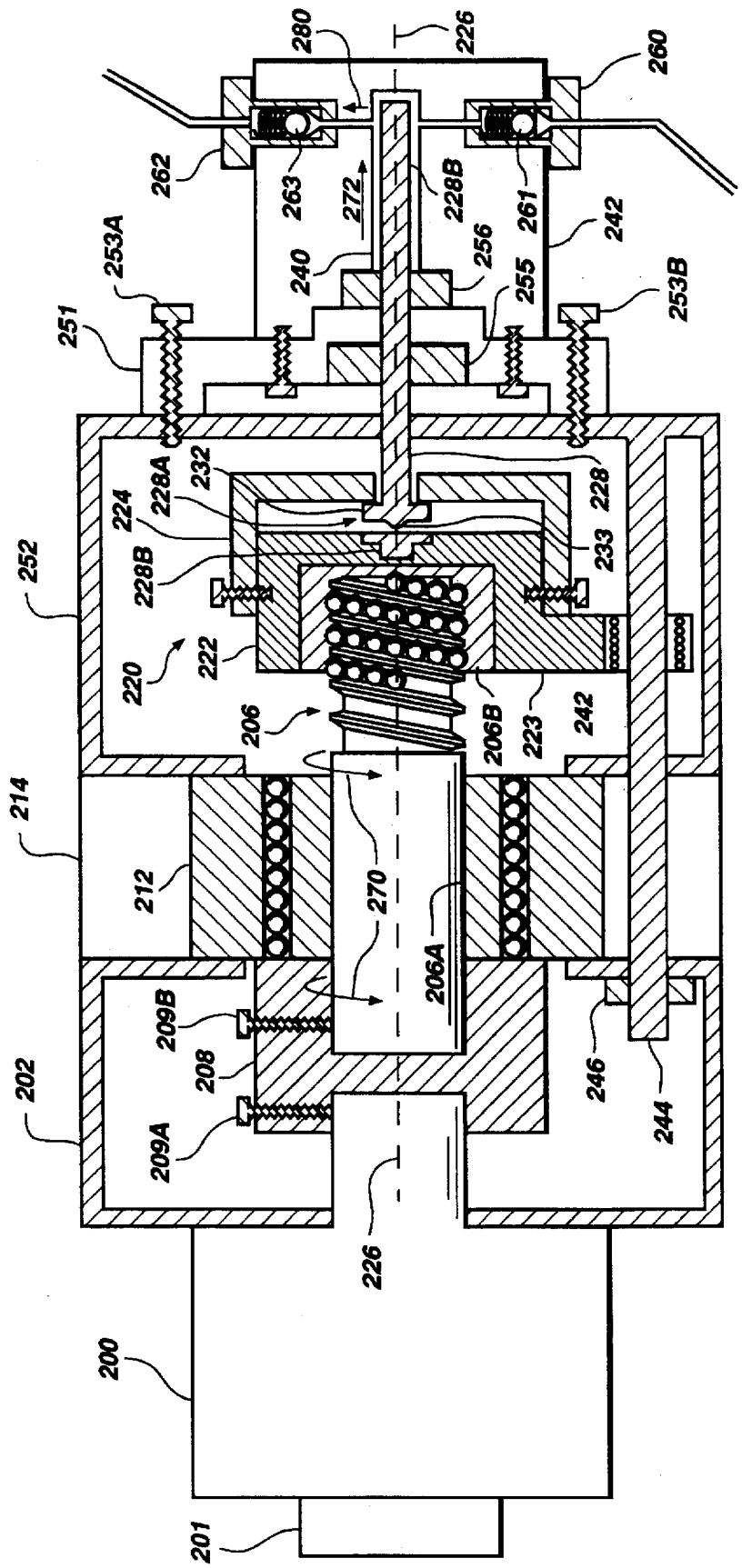
FIG. 2 is a cross sectional view of a preferred embodiment of the linear drive fluid pump.

Piston units 111, 113, 115, 117 each comprise a piston or plunger connected to be driven by the corresponding motor 110, 112, 114, 116, and operably disposed for reciprocating movement in a piston chamber (not shown; see FIG. 2 for an example). Each of piston units 111, 113, 115, 117 is connected by means of a respective inlet valve 140, 142, 144, 146 to receive fluid from one of respective reservoirs 141, 143, 145, 147. The individual reservoirs may contain similar or different samples, as desired by the user. In the illustrated embodiment, inlet valves 140, 142, 144, 146 comprise check valves which open to draw fluid from the reservoir into the piston chamber when suction force exerted by the piston reaches a preset level. Alternatively, inlet valves 140, 142, 144, 146 may comprise positively controlled valves, such as conventional electrically actuated on/off valves or silicon wafer micromachined valves, connected to be operated by system controller 130.

The piston chambers of piston units 111, 113, 115, 117 further have outlet valves 150, 152, 154, 156 through which fluid received from the reservoirs is expelled into respective tubing interfaces 151, 153, 155, 157. In the illustrated embodiment, outlet valves 150, 152, 154, 156 comprise check valves which permit flow of fluid out of the piston chamber when the pressure exerted by the respective piston reaches a preset level. Alternatively, outlet valves 150, 152, 154, 156 may comprise positively controlled valves as described for inlet valves 140, 142, 144, 146.

Tubing interfaces 151, 153, 155, 157 are connected to deliver fluid pumped from respective pumps 100, 102, 104, 106 to a mixing unit 170 having suitable individual inlets (not shown). Mixing unit 170 may be either a dynamic mixer similar to the one depicted in FIGS. 4 and 5 herein, or a static type mixer such as a packed bed, as desired.

Mixing unit 170 has an outlet connected to deliver mixed fluid to solvent delivery means 172, which may be any solvent delivery means suitable for applying the mixed fluid to an analytical unit 174. In the illustrated embodiment, analytical unit 174 is an HPLC column which can be any of the following: fused-silica microbore packed column, glass-lined stainless steel microbore packed column, conventional stainless steel 1 mm, 2 mm, 4.6 mm, 1 cm, 2 cm, 5 cm, or 10 cm packed column. A conventional valve injector such as a Rheodyne injector can be used as solvent delivery means 172. However, analytical unit 174 need not be an HPLC column, but may be any other type of separation or analytic unit requiring flow of a solvent gradient.

Optionally but highly desirably, pulse dampening means 160, 162, 164, 166 are operably disposed upstream of mixing unit 170 for damping pump pulsation in tubing interfaces 151, 153, 155, 157. Suitable pulse dampening means are well-known and commercially available, for example from Hardy and Harman Tube Company. Pulse dampening means 160, 162, 164, 166 are each communicatively connected to be controlled by system controller 130 (shown for pulse dampening means 160 only, for clarity).

Optionally and preferably, pressure transducers 161, 163, 165, 167 may be respectively disposed for sensing the pressure in tubing interfaces 151, 153, 155, 157 upstream of mixing unit 170. Suitable pressure transducers are commercially available, for example the Model SP 70-E from SensoMetrics, Inc., Simi Valley, Calif. Pressure transducers 161, 163, 165, 167 are each communicatively connected to send pressure signals to system controller 130 (for clarity, this is shown for pressure transducer 161 only; transducers 163, 165, 167 are similarly connected.).

For microflow HPLC, a preferred embodiment comprises a high precision motor, pumps having 0.0625 inch diameter pistons, a pulse dampener, a pressure transducer, a micro-volume (e.g. less than 30 μl) dynamic high pressure mixer, a micro-volume internal loop injector, and a microbore column of I.D.≦1 mm.

In a further embodiment, the pumping system may include detection means 180 functionally disposed for detecting chemical components in the output fluid 178 of analytical unit 174. Detection means 180 may comprise probes which detect chemical components by direct contact with the output fluid 178, spectrophotometric detectors which do not require such contact, mass spectrometers, etc., or any combination of these. Detection means 180 may be connected as shown to send data signals reflective of the chemical components via a data acquisition board 190 to system controller 130 via data acquisition means 182. Collection means 184 is desirably connected to analytical unit 174 for collecting the fluid output 178. Collection means 184 may be configured to collect fluid output 178 in bulk, or according to known types of apparatus for collecting separate aliquots selected to isolate individual chemical components appearing in different portions of fluid output 178.

Detection means 180 may alternatively be connected to send all or selected parts of the data signals to an independent computer-based data processing unit. A further option is the provision of recorder means 190 connected to detection means 180 for recording all or selected parts of the data signals. Recorder means 184 may include a visual display of recorded data signals (not shown).

As previously mentioned, pump system controller 130 includes a motion control microprocessor. The motion control processor provides the motor control signals to motor controller 132 according to well-known principles of real-time closed-loop feedback motion control. The flow rate of each individual pump depends on the rate of piston travel, which is controllable by the motion control microprocessor in accordance with signals received from the system controller. Motor controller 132 includes a pulse-width-modulated IC chip for converting the motor control signals to the motor operation signals, which are supplied to motors 110, 112, 114, 116.

Desirably, the motion control feedback system (including the encoder) has a resolution of better than 500 steps per revolution. The preferred number of total steps per piston displacement volume is 3000 to 10000 steps when the fluid pumps of the pump system are constituted by the linear drive pump of FIG. 2. This range of steps provides capability for obtaining a minimum displacement of a 0.0625 inch diameter piston for micro-HPLC to between about 8 nanoliters (abbreviated hereinafter as nl) per step and 2.5 nl per step, respectively.

In the embodiment of FIG. 1, proportioning of solvents for a mixture or a gradient is accomplished by selection of the appropriate proportional flow rates for pumps delivering the respective different solvents to the mixing unit 170. For example, if a mixed fluid containing 10% solvent A/90% solvent B is desired at an output rate of X ml/minute, then pump 100 providing solvent A is operated at a flow rate equal to 0.1X, and pump 102 providing solvent B is operated at a flow rate of 0.9X.

System controller 130 is configured to control the respective flow rates of pumps 100, 102, 104, 106 in a time-varying manner for a constant output flow rate, thereby enabling the production of a gradient output flow. (Output flow rate is defined for purposes of this application as the flow rate of the mixed fluid exiting mixing unit 170.) In a preferred embodiment, system controller 130 is further configured to include a capability of varying the output flow rate both upward and downward by appropriately varying the flow rates of individual pumps. System controller 130 is further desirably constructed to vary the output flow rate for either fixed proportional rates for flow of different solvents, or simultaneously with time variation of the proportional rates of pumps delivering different solvents.

In an alternate embodiment, mixing unit 170 of FIG. 1 is deleted and mixing is accomplished by regulation of a plurality of silicon microvalves to simultaneously deliver the desired proportions of solvents to the piston chamber itself. In such an embodiment, a single pump can replace the four pumps 100, 102, 104, 106 of the embodiment of FIG. 1.

Figure 7:
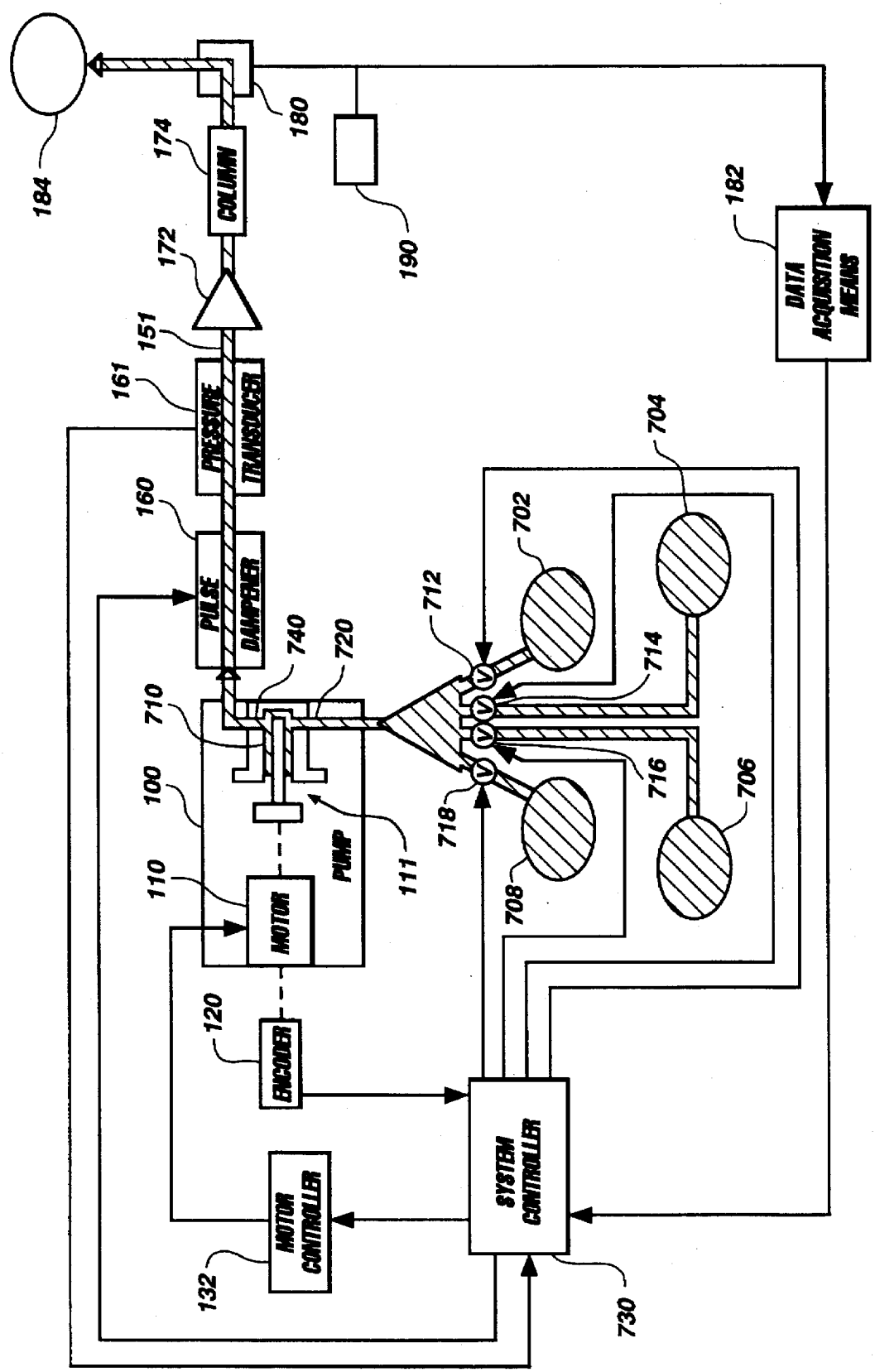
FIG. 7 is a schematic diagram of an embodiment of a linear drive fluid pump having an alternate structure for gradient proportioning.

Referring to FIG. 7, a single pump 700 has a motor 701 and piston assembly 703. Pump 700 is connected to draw fluid into the piston chamber 710 from four different reservoirs 702, 704, 706, 708 through respective microvalves 712, 714, 716, 718. In the stylized depiction of FIG. 7, microvalves 712, 714, 716, 718 are shown feeding into a common inlet 720 of piston chamber 710. In an alternate embodiment (not shown) piston chamber 710 may be provided with four individual microvalve-controlled inlets respectively connected to reservoirs 702, 704, 706, 708.

In either case, microvalves 712, 714, 716, 718 are each operably connected to system controller 730 to receive control signals governing their operation for metering of solvent flow. Each of microvalves 712, 714, 716, 718 is a silicon chip microvalve, which may be an on/off valve operable by direct electrical signalling, by electro-mechanical means such as a piston, or by electro-thermal means, as known in the art for silicon chip valves used in automotive fuel-injection systems (Honeywell, Inc., has developed such devices). Regardless of which valve operation mechanism is used, control signals for operation of microvalves 712, 714, 716, 718 are provided thereto by controller 130, 730, respectively, in the embodiments of FIGS. 1 and 7.

Alternatively, the silicon chip microvalves may be metering-type valves, which are constructed to provide a selectable variable effective aperture which in turn defines corresponding variable fluid transport volumes. Silicon microvalves of dimensions suitable for the embodiment of FIG. 7 may be obtained from Hedco Microengineering Laboratory at the University of Utah, Salt Lake City.

In the embodiment of FIG. 7, system controller 730 is constructed to control any user-selected combination of valves 712, 714, 716, 718 to simultaneously provide respective fluids to piston chamber 710, according to respective individual user-selected transport volumes. Mixing thus occurs within piston chamber 710, which then pumps mixed fluid through outlet 740 to the analytical unit 174 essentially as shown and described for FIG. 1. Outlet valve 740 may be a check valve or a positively-controlled valve, as described for the pump of FIG. 2. System controller 730 is also configured to control both output flow rate at outlet 740 and individual input flows at valves 712, 714, 716, 718 in a time-varying manner.

At present, the embodiment of FIG. 1 is preferred over that of FIG. 7 because commercially available silicon chip valves generally lack sufficient mechanical strength to operate at high pressures for flows in the range of ≦20 ml/minute of the apparatus of this application. However, silicon chip microvalves are being widely researched, and it is believed possible that silicon microvalves having dimensions useful in the instant invention, and of sufficient reliability and precision, will be available in the future.

The linear drive pump design depicted in FIG. 2 provides positive control of the piston in both directions. Accordingly, when pumps 100, 102, 104, 106 of FIG. 1 or pump 100 of FIG. 7 are linear drive pumps, system controllers 130, 730 are further desirably configured to control the corresponding motor(s) 110, 112, 114, 116 to have a fill stroke which is extremely short by comparison with the pump stroke. (Fill stroke refers to leftward movement of piston fluid end 228B in FIG. 2, while pump stroke refers to rightward movement of fluid end 228B).

Optionally and desirably, system controllers 130, 730 are further constructed to provide a prepressurization segment at the beginning of the pump stroke. In the prepressurization segment, there is quick compression of the solvent in the piston chamber to a given pressure that is equal or higher than the inlet pressure downstream at the HPLC column. This prepressurization segment is preferably no longer than about 50 milliseconds. With the pump controller constructed to provide a short fill stroke and a short prepressurization segment time, and further including pulse dampening means immediately downstream of the pump, the pumping system provides substantially pulsation free fluid delivery.

System controllers 130 and 730 can be further constructed to optimize the refill speed and minimize cavitation. The latter is a frequent problem in both conventional cam driven reciprocating pump systems and in syringe pump systems. In a preferred embodiment of the invented pump, cavitation is reduced by providing means for applying pressure on the order of 1 to 10 psi to the solvent reservoir which is connected to the inlet of the piston chamber. Such means for applying pressure may be either pneumatic or hydraulic, or may comprise supplying the solvent from a prepressurized reservoir.

Controller 130 can be further programmed to reproduce a selected initial system pressure and flow rate. Column pressure for the initial solvent composition in a gradient elution protocol can be automatically reset at the completion of each protocol. Alternatively, by downloading the protocol into the CPU the system is rapidly pressurized for the initial solvent composition. The system is then allowed to equilibrate until injection and the starting of the protocol. The rapid pressurization step reduces time fro the regeneration of the initial solvent composition and eliminates "cross-talk" among pump channels if the channel pressures are not equal (this situation can arise when the solvents are of different viscosity). In an automated protocol, the above-described pressurization step is performed automatically each time a protocol is loaded into the CPU. In this way, the initial solvent composition and flow rate can be reliably repeated for sequential runs of a given protocol.

Turning to FIG. 2, a preferred linear drive fluid pump has a motor 200 having a motor shaft 204 which is linearly connected to reciprocate a piston 228 in a chamber 240. Chamber 240 has inlet valve means 260 connectable to receive fluid from a reservoir, and outlet valve means 262 for outputting fluid under pressure. Piston 228 is preferably made of a durable, chemically resistant material. In the illustrated embodiment, piston 228 comprises a zirconium oxide ceramic.

Motor 200 is mounted on a motor bracket 202, and includes an integral optical encoder 201. Preferably, motor 200 is a high torque sensitivity DC brushless servo-motor which has a peak torque of better than 200 oz-in. However, a brushless or brush servo-motor or stepping motor may also be suitable.

A high precision ball screw 206 is coupled to motor shaft 204 through a flex-coupler 208 by means of set screws 209A, 209B (shown in profile) and 210A, 210B (shown head-on). The shank 206A of ball screw 206 passes through and is supported by a ball bearing 212 mounted in a bearing bracket 214, which is affixed to motor bracket 202. Ball screw nut 206B is threadedly engaged with ball screw 206 and is secured to piston mounting means generally indicated at 220.

Piston mounting means 220 includes a coupling bracket 222 attached to the ball screw nut 206B, and a piston retaining bracket 224 secured by screws to the coupling bracket. Retaining bracket 224 has a central portion 224A which is planarly displaced from coupling bracket 222 along the linear axis 226 of piston travel toward the chamber 240, and out of contact with coupling bracket 222. Retaining bracket 224 carries attachment means for attaching a piston 228, described elsewhere herein with reference to FIG. 2A. Piston mounting means 220 slides reciprocatingly within a chamber mounting bracket 252 in precise accordance with the motion of motor shaft 204. Together, flex coupler 208, ball screw 206, and piston mounting means 220 constitute motor connection means for drivingly connecting piston 228 to motor shaft 204.

In the working embodiment, the attachment means carried by retaining bracket 224 is a keyhole 230 in central portion 224A (FIG. 2A). Piston 228 has a drive end 228A (FIG. 2) which is correspondingly configured with a collar 232 whose dimensions are such that drive end 228A can pass through the larger diameter area 230A of keyhole 230, while collar 232 will retain drive end 228A when it is seated in the smaller diameter area 230B. In the latter configuration, piston drive end 228A is thus permitted to slide in keyhole 230 between retaining bracket 224 and coupling bracket 222. This arrangement permits piston 228 to freely float inside the piston mounting bracket, and thus facilitates trouble-free self-alignment with the chamber 240 in the attached chamber housing 250.

Piston drive end 228A is further preferably configured with a convex end surface 233. When the motor shaft 204 drives the ball screw 206 and coupling bracket 222 toward the right-hand side of FIG. 2, the forward surface 222A of the coupling bracket will contact drive end 228A of piston 228 to in turn drive the piston into the chamber 240. Forward surface 222A is desirably provided with an insert 222B of a hard durable material such as steel in the area contacted by drive end 228A of the piston. The convex surface 233 of the piston drive end further facilitates the self-alignment of piston 228 in the chamber.

In a preferred embodiment, coupling bracket 222 has a lower segment 223 having a linear ball bearing 242 which serves as a counter rotation travelling guide for the piston mounting bracket. A steel rod 244 is mounted through linear bearing 242 and secured by a nut 246 to motor bracket 202. Rod 244 may further be secured to chamber bracket 252.

Chamber 240 is formed within a chamber housing 248 affixed to a support spacer 251, which is in turn attached to chamber bracket 252. Chamber bracket 252 is in turn mounted to bearing bracket 214. Together, chamber bracket 252, bearing bracket 214 and motor bracket 202 constitute a pump frame for supporting the operating elements of the pump. In a highly preferred embodiment, chamber housing 248 is detachably mounted to chamber bracket 252, for example with thumbscrews 253A, 253B located in support spacer 251. Desirably, a guide bushing 255 made of a semiresilient material such as a Kel-F or Tefzel high strength fluorocarbon polymer is seated in the opening of chamber 240. The fluid end 228B of piston 228 is inserted through guide bushing 255 and through a high pressure seal 256 into chamber 240. Seal 256 is for maintaining pressure within chamber 240, and may comprise a spring-loaded seal available from Bal Seal Engineering Company of Tustin, Calif.

Movement of piston 228 back and forth along the axis 226 causes fluid to be alternately drawn into chamber 240 from an attached reservoir (not shown) or displaced from chamber 240 through outlet 262. Inlet valve 260 includes a spring-loaded inlet check valve 261. When piston 228 is driven forward by the action of motor shaft 204, fluid in the piston chamber is expelled through a spring-loaded outlet check valve 263 into attached tubing leading to an analytical unit by way of a mixer or other desired components, as shown in FIG. 1. Check valves useful in the inlet 260 and outlet 262 are well known in the art and commercially available.

For solvent pumping at rates below about 30 µl/minute, a spring loaded inlet check valve operable at about 22 psi and outlet check valve operable at about 100 psi are preferred. For reproducible solvent delivery at flow rates below about 50 µl/minute in HPLC, the motor should provide reliable control of the motor speed at a few RPM. To provide a fill stroke time as short as 50 milliseconds at flow rates of 1–20 ml/minute, the motor should be capable of rotational speeds of at least about 4000 RPM.

In the illustrated preferred embodiment, chamber housing 242 and piston 228 are easily detachable from the piston frame and the piston bracket, respectively, and thereby constitute a piston module which can be easily exchanged for a module of like construction but different chamber/piston fluid end dimensions. Alternate piston modules are dimensioned to provide flow rates in a plurality of different flow rate ranges. For example, 0.0625 inch diameter pump-head and piston provides 0.0001 to 1.25 ml/min. flow rate range; 0.125 inch diameter pump-head and piston for 0.01 to 5.0 ml/min. flow rate range; and 0.25 inch diameter pump-head and piston for 0.1 to 20 ml/min. flow rate range. The corresponding volumes of chamber 240 for the above example are 25, 100, and 400 µl, respectively.

Figure 3:
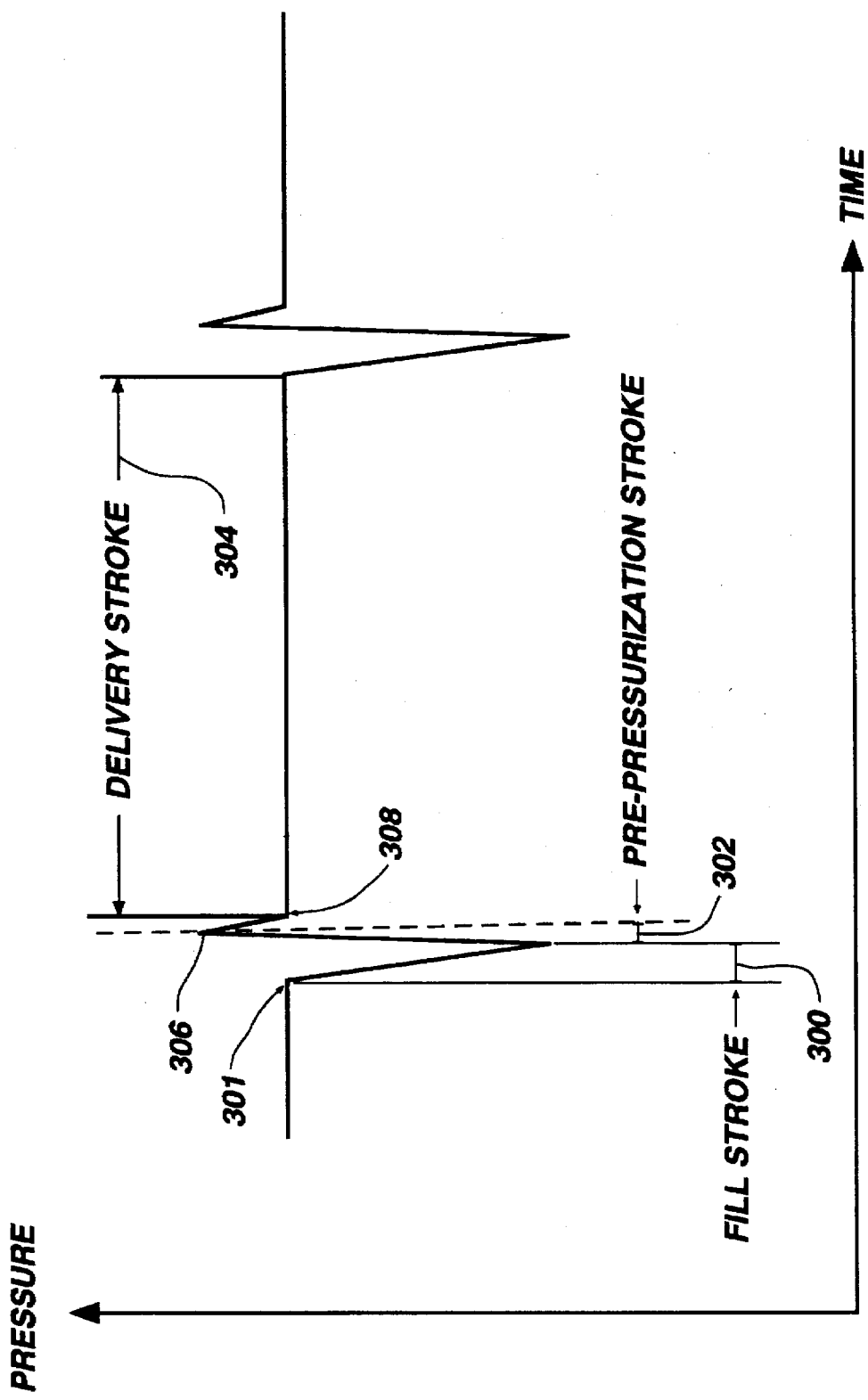
FIG. 3 is a chart illustrating the relative time spans for fill stroke, pre-pressurization stroke, and delivery stroke according to a preferred embodiment.

FIG. 3 illustrates the pressure detected within chamber 240 during a refill stroke, pre-pressurization segment, and delivery stroke cycle, for the pump of FIG. 2. The pressure within the chamber 240 drops to about 20 to 40% of the initial value at the end of a fill stroke 300 of 0.1 second duration. With a rapid pre-pressurization stroke 302 (e.g. 30 msec.) following fill stroke 300, the liquid pressure in chamber 240 reaches a value about 2 to 10% higher than the operational pressure in the delivery stroke 304. The initial pressure over-shoot 306 at the end of the pressurization cycle is allowed to decay rapidly to the operation pressure (the plateau value) during the delivery stroke. The total pulse width of the refill cycle (from the start point 301 of fill stroke 300 to the start point 308 of delivery stroke 304) of 0.1 to 0.15 second, is a high frequency pulse which can be easily dampened by a downstream on-line pulse dampener as illustrated in FIG. 1.

Figure 4:
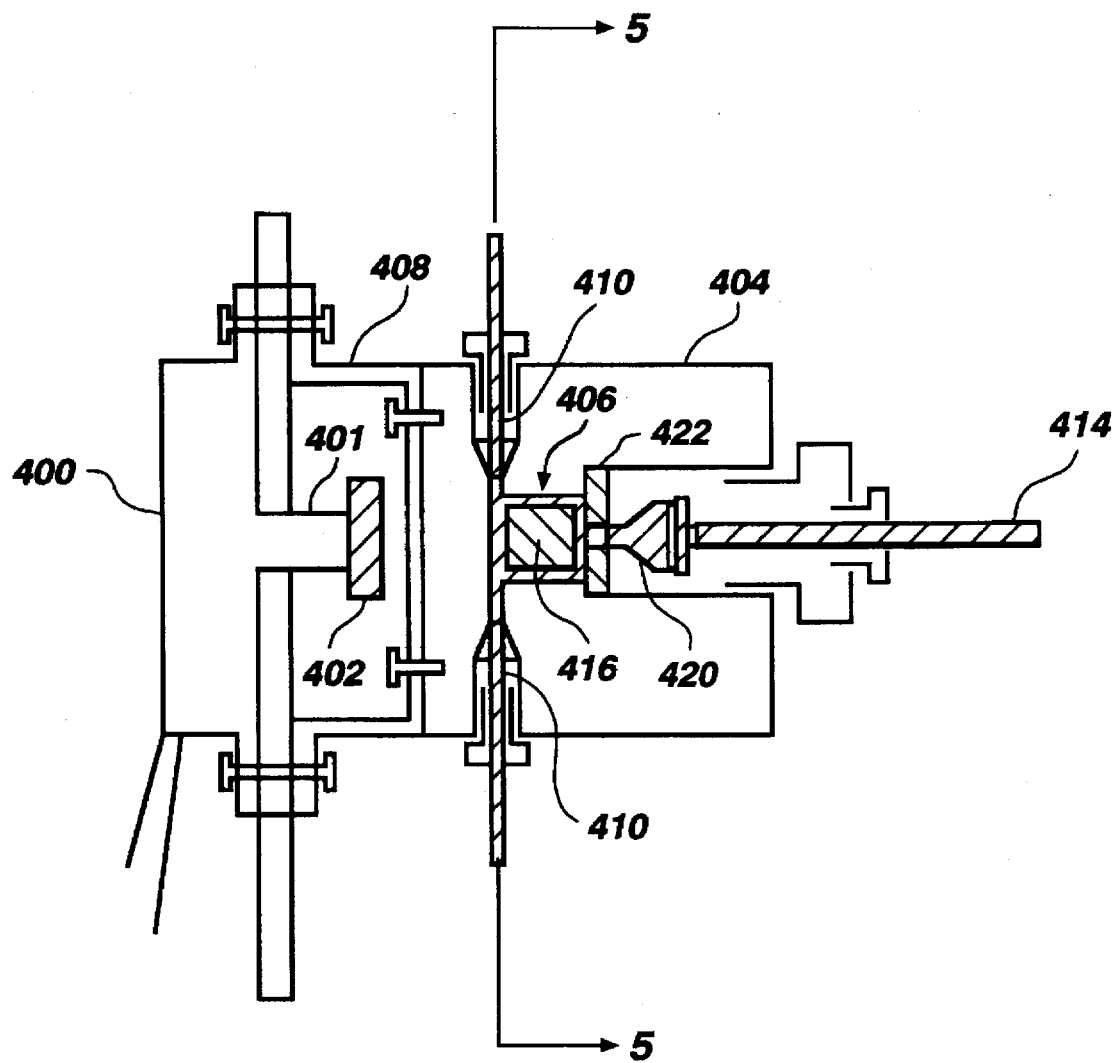
FIG. 4 depicts a high pressure dynamic mixer for binary, ternary, or quarternary gradient elutions.
Figure 5:
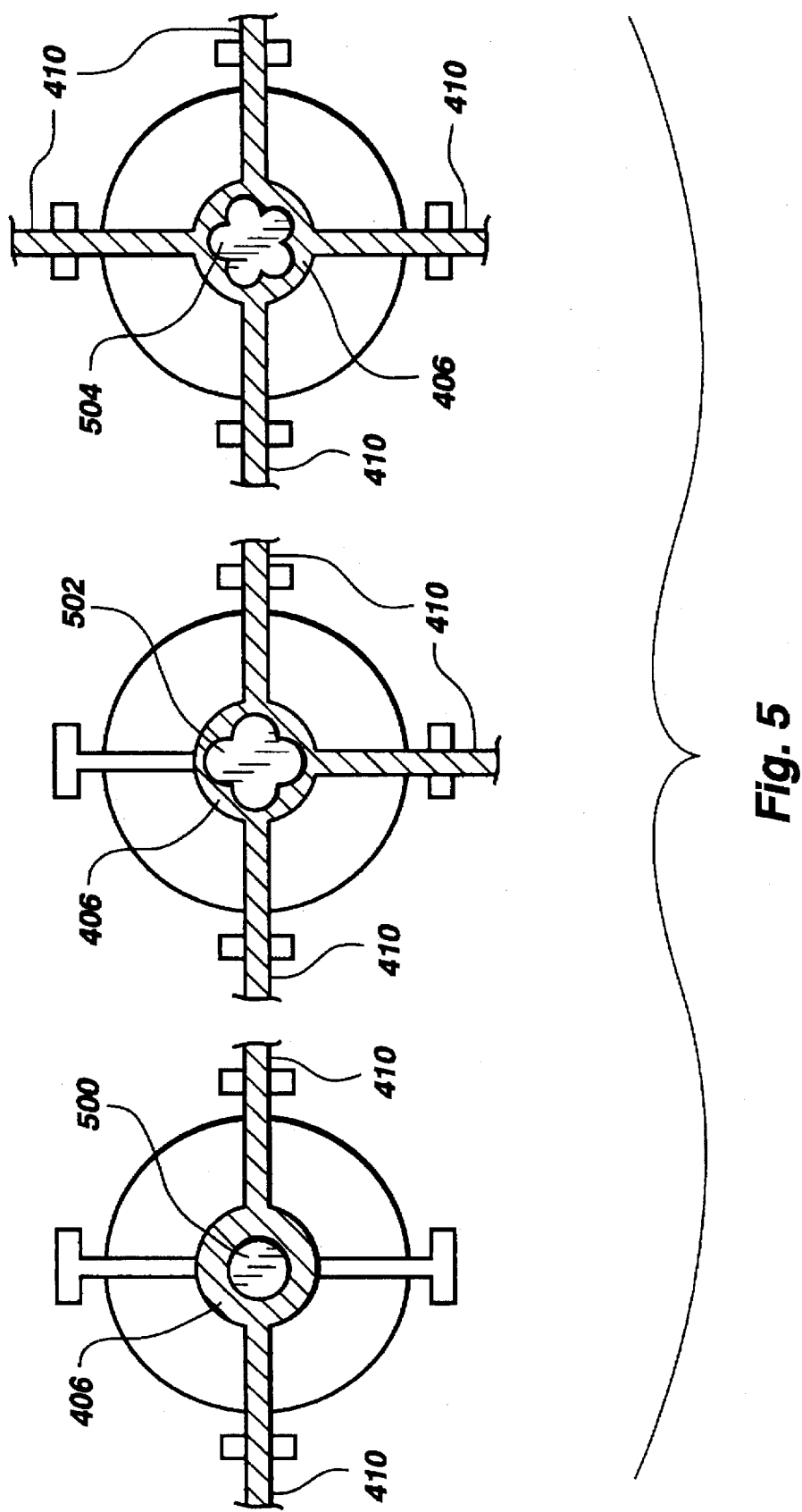
FIG. 5 contains cross-sectional views of mixers for generating binary, ternary, and quarternary solvent gradients.

FIGS. 4 and 5 depict a dynamic high pressure mixer which may be used as mixing unit 170 in FIG. 1. As shown in cross-section in FIG. 4, a motor 400 has a magnet bar 402 attached to the end of motor shaft 401. Motor 400 may be either a DC or an AC motor that has a constant rotation speed of about 100 RPM or higher. A housing 404 formed with an interior mixing chamber 406 is mechanically attached to a bracket 408. Motor 400 is also attached to bracket 408. Mixing chamber 406 is provided with inlet means comprising at least two inlets 410, 412 for connection to individual pumps to receive a different pressurized fluid from each. Outlet means comprising a single outlet 414 is provided for delivering pressurized mixed fluid from the mixer to an analytical unit. Outlet 414 includes an outlet filter 420 which is embedded inside the center core of a washer 422.

As motor shaft 401 rotates, magnetic bar 402 will induce rotation of a magnetic mixing bar 416 positioned within mixing chamber 406. The mixing bar 416 can be designed to various shapes and sizes for better mixing and smaller mixer volume.

Three identical sectional views of the mixer chamber 406 taken along line 5—5 are presented in FIG. 5, differing only in the number of inlets 410 which are receiving fluid as indicated by the hatched stream. Mixing bars 500, 502, 504 are shown having different shapes which may be advantageous for mixing of two, three, or four solvents, respectively, as indicated by the number of inlets 410 receiving fluid flow. The dimensions of mixing bars 500, 502, 504 may also be varied to effectively change the volume of fluid contained in mixer chamber 406.

Figure 6:
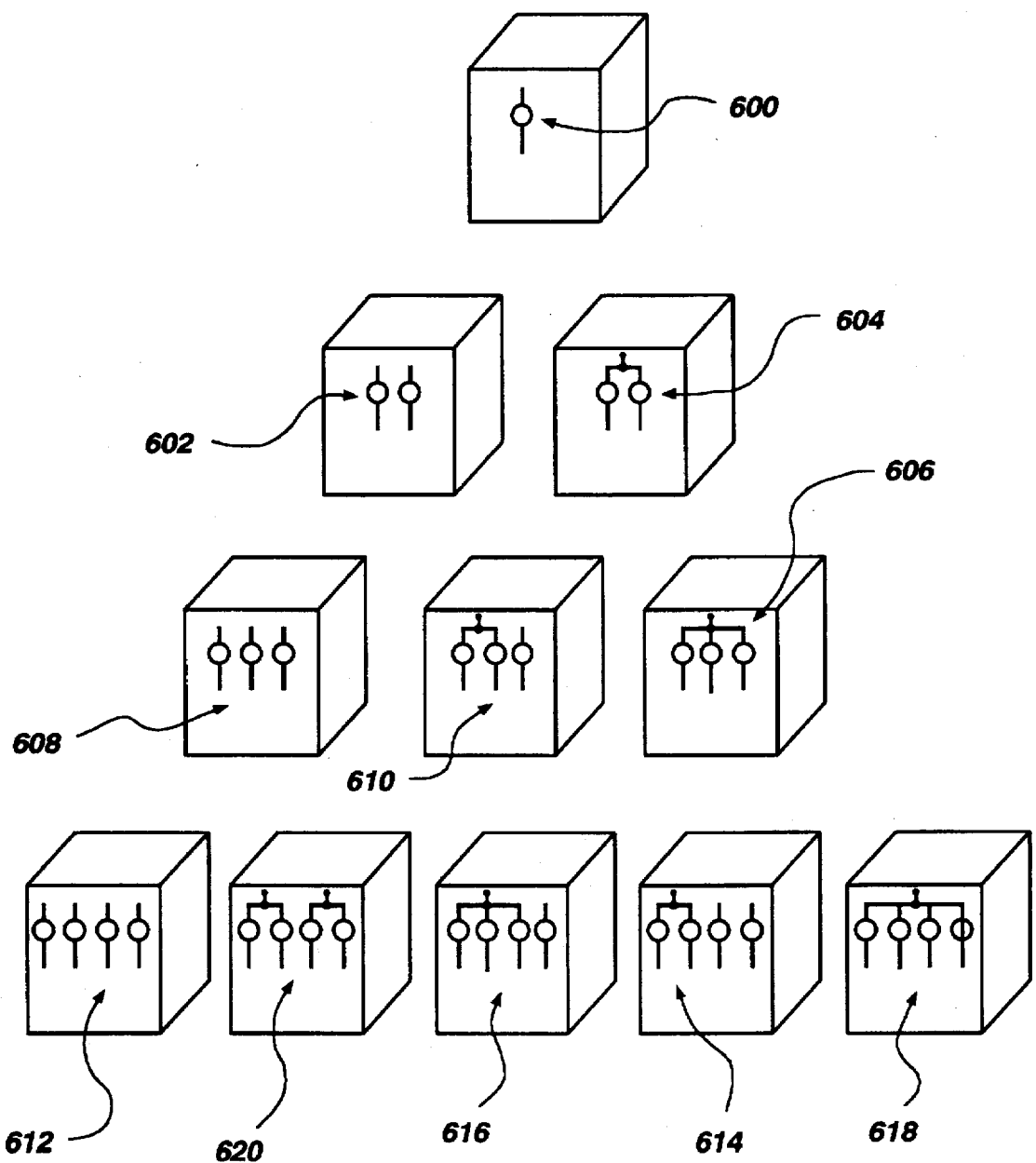
FIG. 6 is a simplified block diagram depicting a plurality of operating modes which can be performed with the multichannel pumping system of FIG. 1.

The operation modes possible with the pump system of FIG. 1 are illustrated in FIG. 6. A single pump pumping system 600 can be used as an isocratic pump for micro-HPLC, analytical-HPLC, and preparative-HPLC using piston and pump-head inner chamber sizes of 0.0625, 0.125, and 0.25 inch diameter, respectively. An additional pump can be mounted on the single pump system to become either a dual isocratic channel pump 602 or a binary solvent gradient pumping system 604. With a properly configured system controller, the dual pump-head pumping system can be used in both gradient and isocratic modes. A three-pump pumping system can be easily obtained by adding one additional pump to the dual pump system. A three-pump system can be operated as a ternary gradient 606, as three isocratic pumps 608, or as a combination of an isocratic and a binary gradient system 610. When a fourth pump is added, producing the embodiment of FIG. 1, the resulting quaternary pumping system can be operated in any of five modes. In isocratic mode 612, the four pump system can replace four isocratic pumps, pumping the same or different fluids. The coupling of two, three or four pumps allows operation in a single binary gradient mode 614, a ternary gradient mode 616, and a quaternary gradient mode 618. The coupling of two dual channel pumps to a dynamic mixer allows a pulseless binary gradient mode 604. Provision of an additional mixer, and coupling two pumps each to the separate mixers, further changes mode 604 to function as dual independent binary gradient pumps (mode 620).

The number of individual pumps in one pumping system is not limited to four and thus even higher orders of gradient capability can be achieved.

Figure 8:
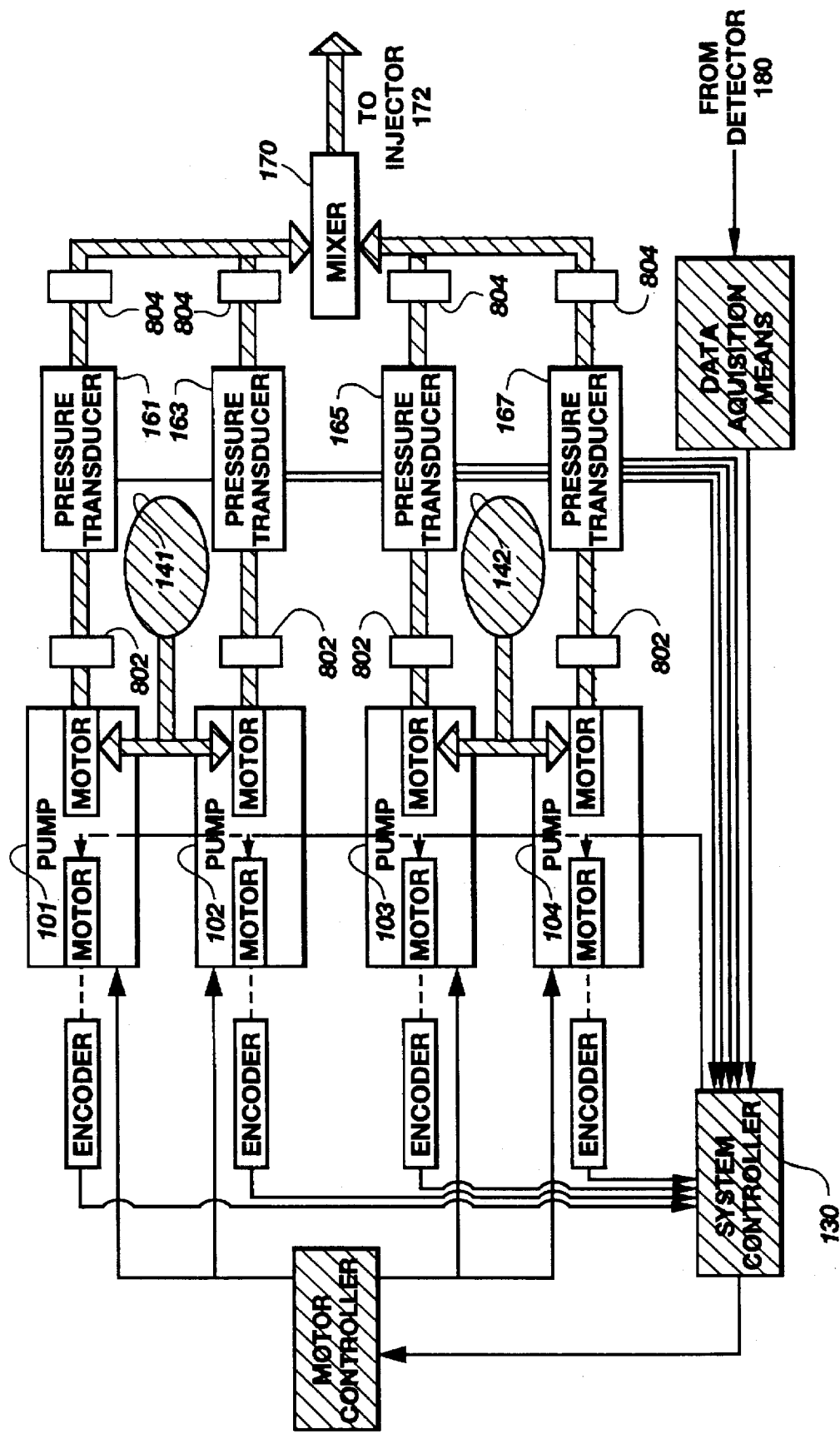
FIG. 8 is a block diagram of another embodiment of the multichannel pumping system.

To reduce or eliminate pulsation at micro-flow rates, it is desirable to either 1) install a small-volume pulse dampener between the pump and the mixer (as shown in FIGS. 1 and 7), or to modify the system as shown in FIG. 8 in which the pulse dampeners 160, 162, 164, 166 are eliminated. In the embodiment of FIG. 8, two pumps 101, 102 are connected to pump the same fluid into a single inlet of mixer 170, and the controller 130 controls pumps 101, 102 to alternate fluid delivery to the mixer in accordance with the readings of the pressure transducers 161, 163 (FIG. 8). That is, when pump 101 completes its outstroke (reaches its point of furthest extension into the piston chamber), pump 102 which is then in a pressurized stand-by state, commences pumping. During the out-stroke of pump 102, pump 101 refills and pressurizes its piston chamber and then holds in standby mode until pump 102 completes its outstroke (reaches the end-position). The alternation of cycles between pumps 101 and 102 is repeated throughout pumping. Similarly, pumps 103 and 104 are connected a single reservoir 142. Pumps 103 and 104 are operated as described for pumps 101, 102 to eliminate pulsation in the output flow. It will be apparent that the improvements illustrated in FIG. 8 can be extended to a system having more than four pumps.

Desirably, controller 130 controls the pumps 101, 102 of FIG. 8 according to a motion control process and a proportion-integration-differential (PID) control algorithm, to provide maximum flow rate stability and prevent flow rate over-shoot and under-shoot. For solvent gradient elution, controller 130 causes rapid pressurization, for example at an initial flow rate of 500 µl/min, of the system to the selected column pressure and at the initial solvent proportions. When the selected column pressure is reached, both solvent A and B are delivered at the flow rates providing the selected solvent proportions at the desired flow rate for the procedure. The desired procedure flow rate may be considerably less than the initial flow rate, for example 50 µl/minute comprising 40 µl/min of solvent A and 10 µl/min of solvent B, to produce a mixture of 80% A:20% B. These values are offered as examples only, and are not limiting.

The above-described rapid column pressurization step is an important step for reducing analysis time and for achieving reproducible results at flow rates in the range of 5–10 µl per minute or below.

Additionally, check valves 802, 804 may be placed in each line between the pump and the pressure transducer and between the pressure transducer and the mixer. Use of a 1024-line optical encoder (as encoders 120, 122, 124, 126 in FIG. 1) provides enhanced resolution for very low flow rates (1 µl/min or less). Alternatively, pressure transducer 161 may be installed in the piston chamber of the pump head. This arrangement provides for rapid monitoring of the system pressure and thus for more accurate control thereof.

Figure 10:
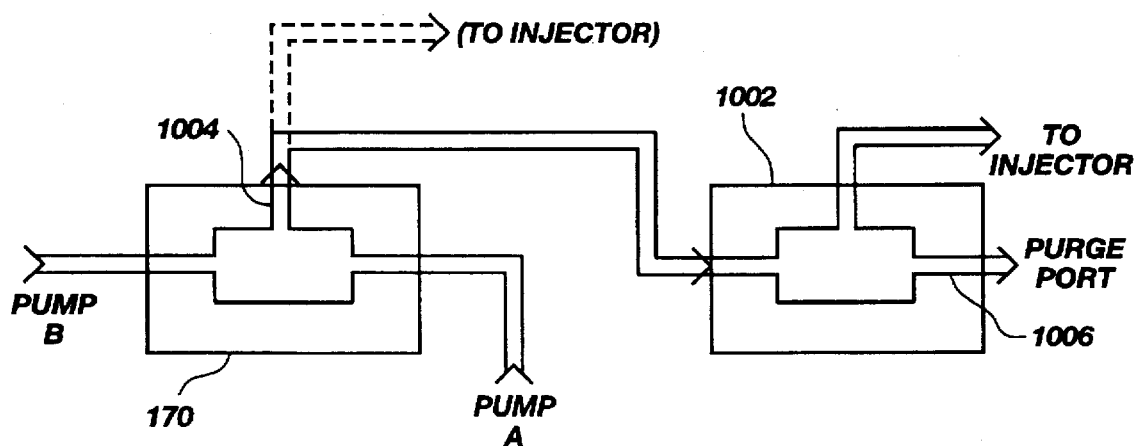
FIG. 10 is a partially exploded side cross-section of an alternate and presently preferred embodiment of a mixing unit of the invention.

A further improvement in gradient mixing capability is provided by the pumping system depicted in FIG. 10. In this system, a secondary mixing unit 1002 is connected downstream in series with the first mixing unit 170. The provision of the secondary mixer enhances the efficiency of mixing at higher flow rates, while retaining the advantages of low void volume and gradient delay times. For example, if a flow rate of 300 µl/min of mixed fluid is desired, ordinarily a chamber of 1 ml volume is needed to obtain adequate mixing. With the two mixers in series, good mixing is obtained with the two chambers each having a volume of only 100 µl. If desired, additional secondary mixers can be added in series to further enhance the mixing capability (not shown). Alternatively, at flow rates below about 30 µl per minute, the outlet 1004 of the primary mixer can be connected directly to the injector, bypassing the secondary mixer. The arrangement of FIG. 10 thus provides great versatility in flow rates.

In the embodiment of FIG. 10, the secondary mixer can be provided with a third port 1006 that can be used as a solvent purge port and/or for splitting the output mixed flow into two streams. Desirably, the third port has a flow restrictor which can be adjusted to a selected split-ratio for splitting of the output flow.

A novel check valve for use in the system is depicted in FIG. 9. A chamber indicated generally at 900 is formed by an upper housing section 902 and a lower housing section 904. The upper and lower housing sections 902, 904 are assembled to form chamber 900 by means of corresponding threaded regions 905. Fluid enters chamber 900 through an inlet 906 and exits through an outlet 908. A poppet 910 is disposed in the chamber along with an O-ring 912 and spring means 914. In the illustrated embodiment, spring means 914 is embodied as a washer-type spring such as a Bellville washer. A filter 920 is also positioned within the housing with a filter portion 922 abutting the lower surface 924 of poppet 910. The filter 920 is here embodied as a frit filter embedded in a PEEK (abbreviation for polyethylene ether ketone) polymer seal.

The lower surface 924 of the poppet has fine grooves 926 which permit fluid to flow around the poppet and through filter portion 922 to outlet 908. Fluid entering through inlet 906 pushes the O-ring, the washer spring and the poppet against the frit filter, and flows through the grooves 926 in the lower surface 924 of the poppet to the outlet 908. Backflow of fluid through the outlet 908 will exert pressure on the lower surface 924 of the poppet, urging it against the O-ring and the top of the chamber thus sealing inlet 906. This check valve design is particularly advantageous for low flow rate, high pressure fluid pumping.

Preferably, the poppet is made of a non-corroding metal or ceramic material. The O-ring is made of a conventional inert resilient material. A polymer sealing disk may be substituted for the conventional O-ring.

A further improved mixer has the magnetic stirring bar coated with a ceramic instead of Teflon. A coating is needed to prevent corrosion of metal stir bars. Typically, such stir bars are coated with Teflon, which wears and sheds fine particles with extended use. The fine particles shed due to the wear on the Teflon cause clogging problems, especially in a system operating at microflow rates. In contrast, ceramic-coated stir bars are much more durable and do not shed particles that cause clogging. A suitable coating is a zirconium oxide ceramic. Sapphire Engineering, Inc., of North Falmouth, Mass., has prepared prototype stir bars with the ceramic coating.

An alternate and presently preferred embodiment of a check valve 930A is depicted in FIG. 9A. In this embodiment, a poppet 932 has a first arm 934, a second arm 936, and a transverse midsection 938. A pair of resilient compressible annular members 944, 946 are respectively seated about the first and second arms 934, 936. Annular members 944, 946 are formed of a durable resilient rubber, resilient plastic, or like elastomeric or resilient material, and are constructed to be sufficiently compressible to serve as effective seals. In the working embodiment depicted in FIGS. 9A, 9B, annular members 944, 946 are shown to be conventional O-rings. The second arm 936 is desirably truncated or otherwise configured to be somewhat narrower than the first arm 934, to create a space to accommodate fluid on the downstream side of the poppet. Also, the transverse midsection 938 has a trough 948 formed on the surface 938A, to one side of the first and second arms 934, 936. The trough 948, or a similar groove or notch, is needed to facilitate fluid flow about the poppet into the region abutted by surface 938A and thence out through the outlet 950.

The first and second arms 934, 936 are of length L1 or L12 (FIG. 9A) which is slightly shorter than the uncompressed thickness T of the respective annular members 944, 946. In the check valve with the poppet thus constructed, when forward flow (flow in the desired direction) exerts pressure on surface 938B of the transverse midsection and pushes the second arm 936 against the outlet 950, the annular member 946 is slightly compressed, but the trough 948 and the truncated width W2 of arm 936 allow fluid to flow past the annular member 946 and through the outlet 950. Conversely, backflow through the valve is prevented: when fluid pressure is exerted on the side 938A of the poppet, the first arm 934 is urged against the inlet and compresses the annular member 934 which seals against both the arm 934 and the housing, and thus prevents backflow through the inlet 954. The check valve having elastomeric annular members 944, 946 on both sides of the poppet provides a very fast response to changes in direction of pressure acting on the poppet, and is therefore highly preferred. However, it is within contemplation that a simplified embodiment of the check valve would have only a single annular member.

The downstream outlet 950 passes through a washer seal 952, which in a working embodiment is formed of PEEK (polyethylene ether ketone) plastic, seated in the chamber 944. Fluid filtering means here embodied as a frit 956 is desirably provided in the washer seal 952, or otherwise disposed to cover the end 950A of the outlet 950, to trap any particulates. The frit used in the working prototype is a 3/16" sintered stainless steel frit. However, frits made of other materials such as PEEK or other plastics or polymers, or of ceramic, could also be used.

Figure 12:
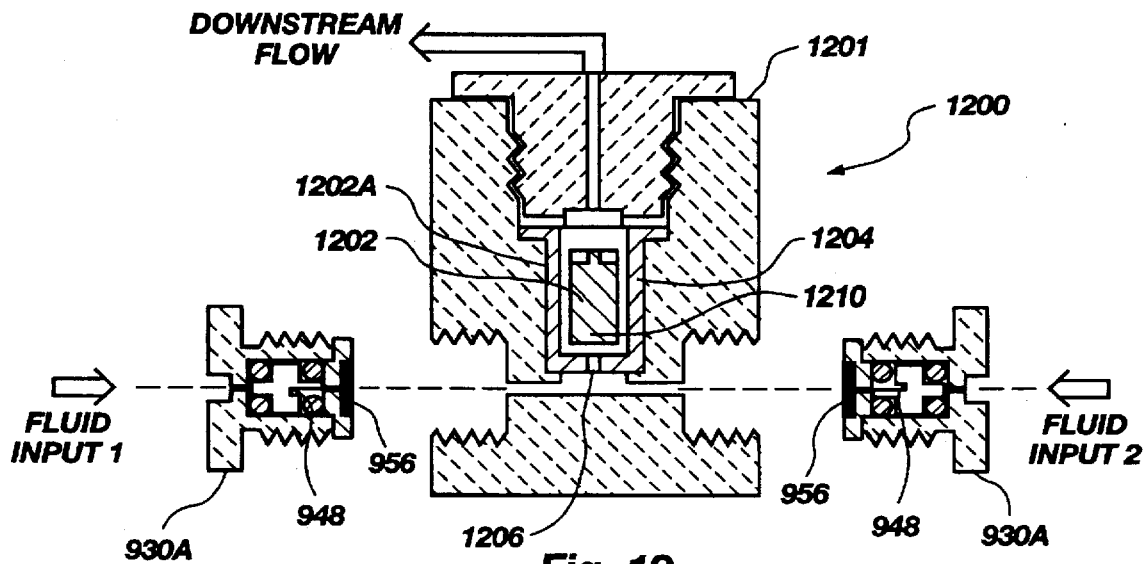

The check valve of FIG. 9A is an embodiment especially intended for use in the inlets to a mixer, as shown in FIG. 12.

In an alternate embodiment (FIG. 9C), the orientation of the poppet 932 with respect to the washer seal 952 and the fluid filtering means (frit 956) is reversed. In reversing the poppet orientation, the check valve operation is thus changed, now preventing backflow through the orifice 964 while permitting flow through orifice 960. This embodiment is useful in the outlet line of a pump head, as shown in FIG. 11.

Figure 11:
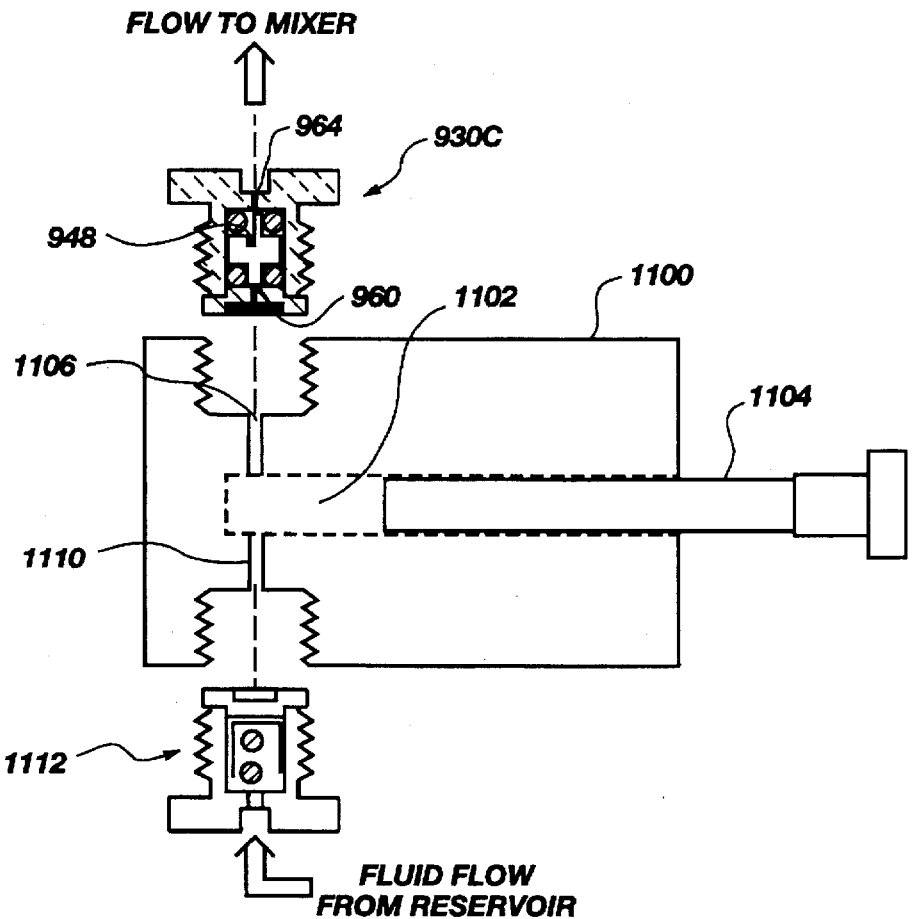
FIG. 11 is a partially exploded side cross-section of a piston chamber assembly of a fluid pump incorporating the check valve of FIG. 9C.

As shown in FIG. 11, a fluid pump desirably incorporates the check valve 930C of FIG. 9C in the outlet flow line. A basic fluid pump comprises a housing 1100 defining a piston chamber 1102 having a piston 1104 disposed therein, the piston being operably connected to a motor (not shown) and driven thereby in a reciprocating motion. The outlet 1106 from the piston chamber 1102 has the check valve 930C disposed therein. The inlet 1110 also has a check valve 1112 disposed therein, however, this check valve may be a conventional ruby ball-type check valve. Alternatively, the inlet 1110 may also have a check valve 930A disposed therein.

By using the check valve 930C having a frit on the upstream side of the check valve, the check valve is rendered considerably more durable and requires replacing, if at all, far less frequently than a conventional check valve. Failure of conventional check valves is a common problem in the operation of fluid pumps, especially those operating at high pressures. Particulates entering the check valve chamber from the piston chamber tend to chew up the resilient members, or tend to deposit on the ruby ball so that it does not seal well. As a result the check valve eventually becomes leaky and has to be replaced. The check valve including the filtering means disposed upstream of the valve chamber is sufficiently resistant to particulate friction to constitute an essentially permanent check valve.

Figure 9D:
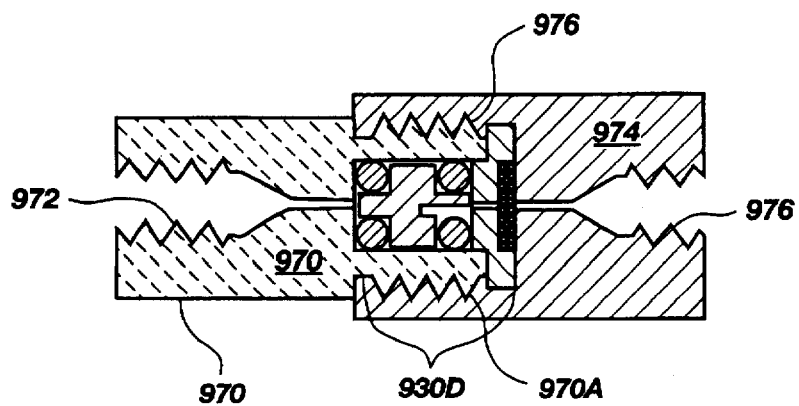
FIG. 9D depicts another alternate embodiment of a check valve.

In another embodiment, a check valve similar to check valve 930A has a housing configured to permit the check valve to be installed in-line in the tubing of a pumping system (FIG. 9D). The in-line check valve assembly is useful to help ensure one-way flow in the flow stream. In the embodiment depicted in FIG. 9D, the check valve portion 930D is disposed in one end of a first housing segment 970, while the other end 970A of the housing segment has an internal threaded region 972 for mating with an attachment fixture on a tubing (not shown). A second housing segment 974 is mounted via a first internal threaded region 976 about corresponding threads formed on the exterior of end 970A of the first housing segment. Second housing segment 974 also has a second internally threaded region 976, for mating with an attachment fixture on a tubing (not shown).

While in the embodiment of FIG. 9D the housing segments 970, 974 are shown as being threadedly mated together, and with threaded regions for mating with certain standard tubing attachment fixtures, numerous alternate configurations for mating the two housing segments and for attaching the housing segments to the tubing. For example, instead of having corresponding internal and external threads, the two housing segments 970, 974 could be fixed together with a set screw or by a frictional bushing or other type of frictional fitting. Instead of the internally threaded regions 972, 976, a frictional bushing or fitting could be used, for example similar to those commonly used for attaching syringe barrels to needles or tubing.

An improved and presently preferred embodiment of a high pressure mixing unit 1200 is depicted in FIG. 12. In this embodiment, a housing 1201 which is typically formed of stainless or inert steel defines a mixing chamber 1202. The interior wall 1202A of the mixing chamber is provided with a very smooth polymer lining or shield, here shown as a cup 1204 formed of PEEK plastic, to reduce formation of particulates produced by frictional wear between the magnetic rotor and the chamber surface. The cup 1202 has an opening 1206 registered with the inlet. PEEK is a solid, chemically inert plastic which can be machined to provide an extremely smooth surface that has been found to reduce or eliminate frictional wear problems from the rotor 1210 in the mixer. Where a conventional TEFLON-coated rotor is used in a stainless-steel chamber, the chamber walls have just sufficient roughness to chew up the TEFLON coating, producing fine particulates which clog the flowstream, especially in a micro-flow rate apparatus. These particulates also may appear as impurities in a chromatogram, or otherwise interfere with the flow so as to introduce anomalies into the chromatogram. Where the rotor is coated with ceramic, the ceramic is harder than the stainless steel and causes particulates to be rubbed off the chamber surface. These ceramic-derived particulates cause problems similar to those described for TEFLON-derived particulates. The PEEK cup has been found to substantially eliminate the problems resulting from particulate formation by friction between the rotor and the chamber wall. PEEK is the presently preferred material; the cup is constructed by machining of PEEK blanks to the desired dimensions and to provide the inlet opening. However, it is believed that other polymer materials, such as TEFLON, polypropylene, polyethylene, polyphenylene sulfate, VESPEL, or KYNAR would also provide good results.

Other methods of manufacturing a polymer lining for the chamber are contemplated. For example, the polymer material could be prepared in a mold directly to the desired shape, with or without subsequent machining. The polymer material could conceivably also be molded within the chamber itself, again either with or without subsequent machining to further refine the configuration and dimensions of the lining.

Further desirably, the mixing unit incorporates a check valve 930A of FIG. 9A in the inlet line(s) from the upstream fluid sources.

The chromatography pumping system described is capable of reproducibly and accurately achieving step gradient changes of 20% at 50 µl per minute. The pumping system also provided substantially linear 0–100% gradients at flow rates of 5 to 100 µl/minute and pressures of up to about 10,000 psi.

From the above description, it will be apparent that the pumping system and the linear drive fluid pump of this invention have numerous advantages. Since the total liquid end volume of the pump including piston, inlet check valve, outlet check valve, pulse dampener, pressure transducer, and interface tubings is upstream of the proportioning and mixing unit, gradient linearity, gradient delay time, and gradient regeneration time are unaffected by a large liquid end volume.

Furthermore, the multi-channel pump system is capable of being operated as a multi-channel isocratic pump, or as binary, ternary, or quarternary gradient pumps. The pumping system including at least four individual pumps can be controlled from a single personal computer or the like. Constant flow rates in a range from about 0.1 µl/minute to about 20 ml/minute at pressures of 10 to 10,000 psi are provided by the linear drive fluid pump having interchangeable piston modules. A single multi-channel pump system including the invented fluid pump is thus useful for HPLC with microbore columns of I.D.$\leq 1$ mm, analytical columns which generally have an I.D. of between about 1 mm and 4.6 mm, and for preparative-scale-applications with columns of I.D. at least 10 mm. Preparative output potentially as large as 80 ml/minute is readily obtained by operating all four pumps at 20 ml/minute together as an isocratic pump. The latter preparative capacity is about eight times greater than that available with typical prior art HPLC apparatuses.

In addition to providing excellent flow rate control and range capacity, the linear drive fluid pump is extremely simple and durable. The design having a floating mount connecting the piston to the linear actuator, and the point contact between the motor coupling and the convex end of the piston, provide for self-aligning of the piston during operation which reduces wear and breakage thereof. The flex coupling to the linear actuator further reduces alignment problems and strain on key moving parts.

Although the multichannel pump system and the linear drive fluid pump are described primarily with reference to HPLC, their uses are not limited to HPLC and may include the following: super-critical fluid chromatography, super-critical fluid extraction, and capillary electrophoresis; or any other technology where multichannel high-pressure fluid delivery and/or accurate, low flow rates are desired.

What is claimed is:

1. A fluid pump, comprising:
   a housing defining a piston chamber;
   a piston slidably disposed in said chamber;
   motor means operably linked to said piston for driving said piston;
   an inlet in said housing for receiving unpressurized fluid into said piston chamber;
   an outlet in said housing for discharging fluid from said piston chamber under pressure; and
   a check valve operably disposed in said inlet to prevent backflow of fluid, and comprising:
     a valve housing defining a valve chamber,
     a first orifice in said valve housing, configured to connect to receive fluid from an external reservoir,
     a second orifice connected for fluid flow downstream through said inlet into said chamber,
     poppet means disposed in said valve chamber and configured to permit said downstream fluid flow while preventing backflow, said poppet means comprising:
       a poppet configured with a midsection having first and second sides, dimensioned to occlude said valve chamber, and configured to provide fluid flow from said first side to said second side; a first arm extending transversely from said midsection first side toward said first orifice, dimensioned to occlude said first orifice, and having a first arm length; and a second arm extending transversely from said midsection second side toward said second orifice, said second arm being configured and dimensioned to partially occlude said second orifice while being retained in said valve chamber, and having a second arm length;
     a first seal annularly disposed about said first arm, formed of a resiliently compressible material, and having an uncompressed thickness which is slightly greater than said first arm length; and
     a second seal annularly disposed about said second arm, formed of a resiliently compressible material, and having an uncompressed thickness which is slightly less than said second arm length; and
     fluid filtering means disposed in said valve housing over said first orifice for filtering fluid entering said valve chamber.

2. The fluid pump of claim 1, wherein said piston chamber and said piston are dimensioned, and said motor is constructed to operate at a speed sufficient, to provide pumping rates between about 0.1 µl per minute and about 20,000 µl per minute.

3. The fluid pump of claim 1, wherein said motor is constructed to operate at a speed sufficient to drive said piston to pump said fluid at a pressure of up to at least about 10,000 psi.

4. The fluid pump of claim 1, wherein said first and second seals are O-rings.

5. A check valve, comprising:
   a housing defining a chamber, and having first and second orifices on opposing sides of said chamber;
   a poppet disposed within said chamber, and comprising:
     a midsection having first and second sides, dimensioned to occlude said chamber, and configured to provide fluid flow from said first side to said second side;
     a first arm extending transversely from said midsection first side toward one of said orifices, dimensioned to occlude said one orifice, and having a first arm length,
     a second arm extending transversely from said midsection second side toward the other of said orifices, configured and dimensioned to partially occlude said other orifice while being retained in said chamber, and having a second arm length;
   a first seal annularly disposed about said first arm, formed of a resiliently compressible material, and having an uncompressed thickness which is slightly greater than said first arm length; and
   a second seal annularly disposed about said second arm, formed of a resiliently compressible material, and having an uncompressed thickness which is slightly less than said second arm length.

6. The check valve of claim 5, wherein said poppet is oriented in said chamber with said second arm partially occluding said second orifice, and wherein said said second orifice is an outlet and said first orifice is an inlet.

7. The check valve of claim 6, further including fluid filtering means mechanically adapted to said housing over said outlet, for filtering fluid flowing downstream through said outlet.

8. The check valve of claim 5, wherein said said poppet is oriented in said chamber with said second arm partially occluding said second orifice, and wherein said second orifice is an inlet and said first orifice is an outlet.

9. The check valve of claim 8, further including fluid filtering means mechanically adapted to said housing over said inlet, for filtering fluid entering said chamber through said inlet.

10. The check valve of claim 5, wherein said first and second seals are O-rings.

11. The check valve of claim 5, wherein said housing comprises a cup-shaped portion having a bottom with one of said orifices formed therein and an upper end, and a cap formed of a rigid or semi-rigid plastic sealingly seated over said upper end and having the other of said orifices formed therein.

12. The check valve of claim 11, further including filtering means disposed in said cap over said other orifice for filtering fluid passing through said other orifice.

13. The check valve of claim 5, which is constructed to prevent backflow at pressures of up to at least about 10,000 psi.

14. The check valve of claim 13, which is dimensioned for a fluid flow rate which is between about 0.1 per minute and about 20,000 µl per minute.

15. The check valve of claim 5, wherein said midsection has a groove formed on said second side.

16. The check valve of claim 5, wherein said housing is configured to permit said check valve to be installed in-line in a pumping system.

17. The check valve of claim 5 wherein said first and second seals are made of an elastomeric material.

18. The check valve of claim 5 wherein said check valve is associated with a pulse-dampening system.

19. A mixing unit for mixing one or more fluids received from a pump, comprising:
    a housing made of a first material, having an inner surface which defines a mixing chamber;
    an inlet formed in said housing for fluid communication between an upstream fluid flow line and said mixing chamber;
    an outlet formed in said housing for discharging mixed fluid;
    a magnetic rotor disposed in said mixing chamber for rotation by a magnetic rotational drive unit, said rotor having an exterior surface formed of a second material; and
    a check valve installed in said inlet, said check valve comprising:
        a valve housing defining a valve chamber, and having a valve inlet connectable to receive fluid flow and a valve outlet disposed for fluid communication with said valve chamber;
        a poppet disposed within said valve chamber, and comprising:
            a midsection having first and second sides, dimensioned to occlude said valve chamber, and configured to provide fluid flow from said first side to said second side;
            a first arm extending transversely from said midsection first side toward said valve inlet, dimensioned to occlude said valve inlet, and having a first arm length,
            a second arm extending transversely from said midsection second side toward said valve outlet, configured and dimensioned to partially occlude said valve outlet while being retained in said chamber, and having a second arm length;
            a first seal annularly disposed about said first arm, formed of a resiliently compressible material, and having an uncompressed thickness which is slightly greater than said first arm length; and
            a second seal annularly disposed about said second arm, formed of a resiliently compressible material, and having an uncompressed thickness which is slightly less than said second arm length.

20. The mixing unit of claim 19, which is constructed for use with fluid pressure of up to at least about 10,000 psi within said mixing chamber.

21. The mixing unit of claim 19, which is dimensioned for a fluid flow rate which is between about 0.1 per minute and about 20,000 µl per minute.

22. The mixing unit of claim 19, wherein said first material is steel and said second material is selected from the group consisting of: TEFLON and ceramic.

23. The mixing unit of claim 19 wherein said housing has lining means disposed on the inner surface for preventing frictional contact between said first material and said second material, said lining means formed of a third material selected for frictional compatibility with said second material.

24. The mixing unit of claim 23, wherein said third material is selected from the group consisting of: polyethylene ether ketone, TEFLON, polypropylene, polyethylene, polyphenylene sulfate, VESPEL, and KYNAR.

* * * * *

UNITED STATES PATENT AND TRADEMARK OFFICE
CERTIFICATE OF CORRECTION

PATENT NO. : 5,664,938
DATED : September 9, 1997
INVENTOR(S) : Yang

It is certified that error appears in the above-identified patent and that said Letters Patent is hereby corrected as shown below:

On page 1 of the cover pages, under "Other Publications," column 2, line 14, change "Fused-Solica" to --Fused-Silica--;

On page 2 of the cover pages, under "Other Publications," column 2, line 6, change "Packed-Col.-High-:erformance" to --Packed-Column High-Performance--;

In column 2, line 39, change "time" to --times--;

In column 8, line 56, change "pump 100" to --pump 700--;

In column 9, line 29, change "fro" to --for--;

In column 11, line 14, change "242" to --248--;

In column 14, lines 43-44, change "L1 or L12" to --L1 & L2--;

In column 14, line 56, change "member 934" to --member 944--;

In column 15, line 2, change "944" to --900--;

In column 16, line 15, change "cup 1202" to --cup 1204--;

In column 19, line 12, after "0.1" insert --$\mu$1--; and

In column 20, line 27, after "0.1" insert --$\mu$1--.

Signed and Sealed this

Nineteenth Day of January, 1999

*Attest:*

*Attesting Officer*

*Acting Commissioner of Patents and Trademarks*